(12) United States Patent
Takahashi

(10) Patent No.: US 8,094,776 B2
(45) Date of Patent: Jan. 10, 2012

(54) TOMOSYNTHESIS RADIOGRAPHING APPARATUS

(75) Inventor: Kenji Takahashi, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 34 days.

(21) Appl. No.: 12/585,885

(22) Filed: Sep. 28, 2009

(65) Prior Publication Data

US 2010/0080342 A1    Apr. 1, 2010

(30) Foreign Application Priority Data

Sep. 29, 2008 (JP) ................................. 2008-250276

(51) Int. Cl.
*A61B 6/02* (2006.01)
(52) U.S. Cl. ........................................... 378/21; 378/36
(58) Field of Classification Search .................... 378/21, 378/22, 36
See application file for complete search history.

(56) References Cited

U.S. PATENT DOCUMENTS

| 5,812,629 | A | 9/1998 | Clauser |
| 7,180,979 | B2 | 2/2007 | Momose |
| 2003/0133747 | A1 | 7/2003 | Schmitt |
| 2006/0045234 | A1* | 3/2006 | Pelc et al. .......................... 378/9 |
| 2007/0009088 | A1* | 1/2007 | Edic et al. ........................ 378/62 |
| 2007/0183583 | A1* | 8/2007 | Baumann et al. ............. 378/145 |
| 2007/0280408 | A1* | 12/2007 | Zhang ............................. 378/25 |

FOREIGN PATENT DOCUMENTS

| JP | 2006-259264 | 9/2006 |
| JP | 2007-203062 | 8/2007 |
| JP | 2007-203063 | 8/2007 |
| JP | 2007-206075 | 8/2007 |

* cited by examiner

*Primary Examiner* — Glen Kao

(74) *Attorney, Agent, or Firm* — Jean C. Edwards, Esq.; Edwards Neils PLLC

(57) ABSTRACT

Providing a radiation emission unit having multiple radiation sources for emitting radiation onto a subject, in which the multiple radiation sources are distributed such that the radiation emitted from each radiation source and transmitted through the subject forms a part of a projected image of the subject. Each radiation source is a source that emits fan beam radiation and is disposed such that a plane of the fan beam having a wider spread angle intersects with an arrangement direction of the multiple radiation sources and is arranged parallel to each other.

7 Claims, 24 Drawing Sheets

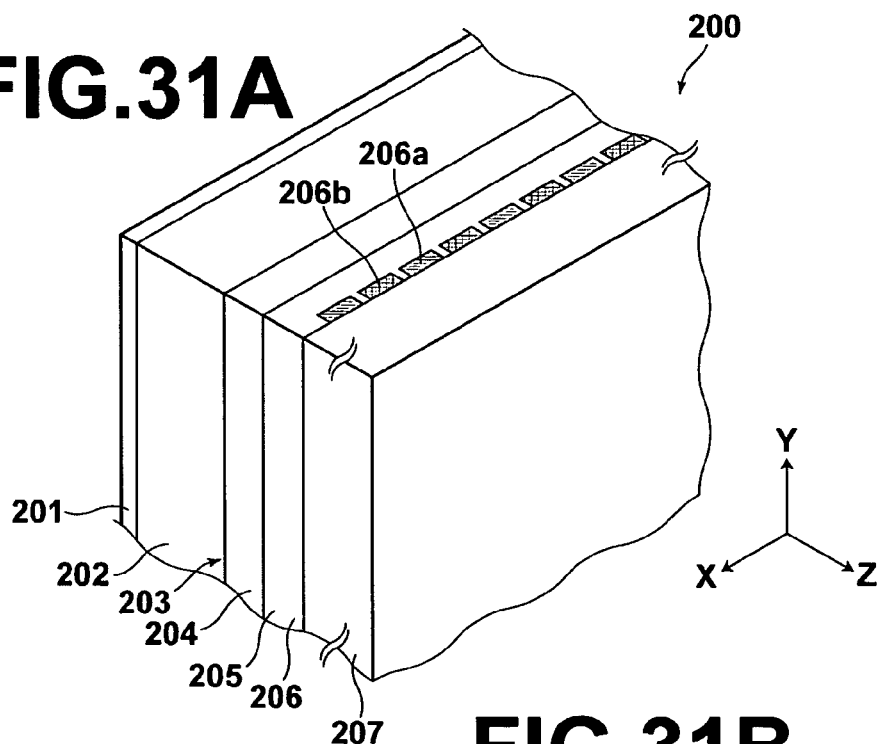
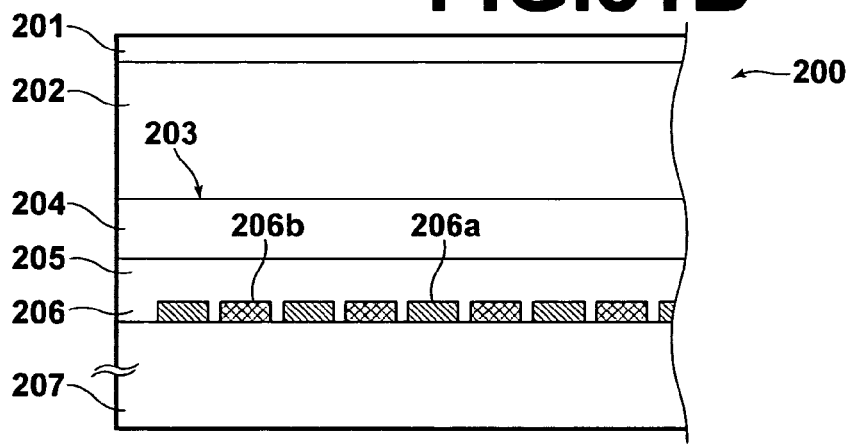
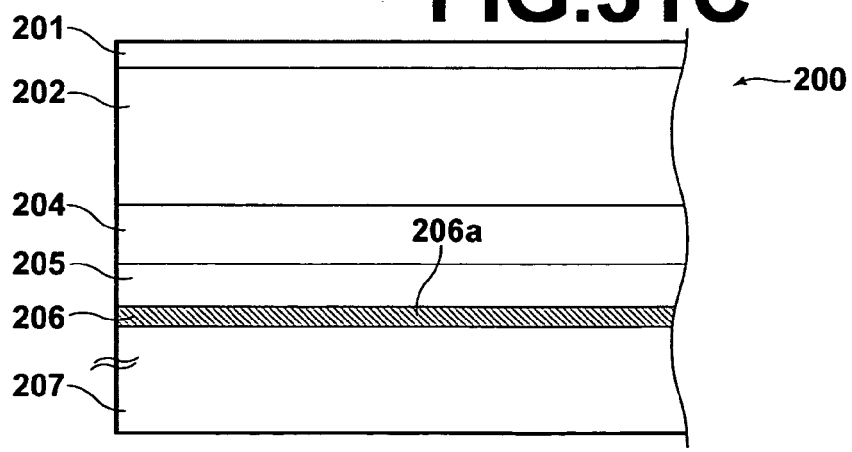

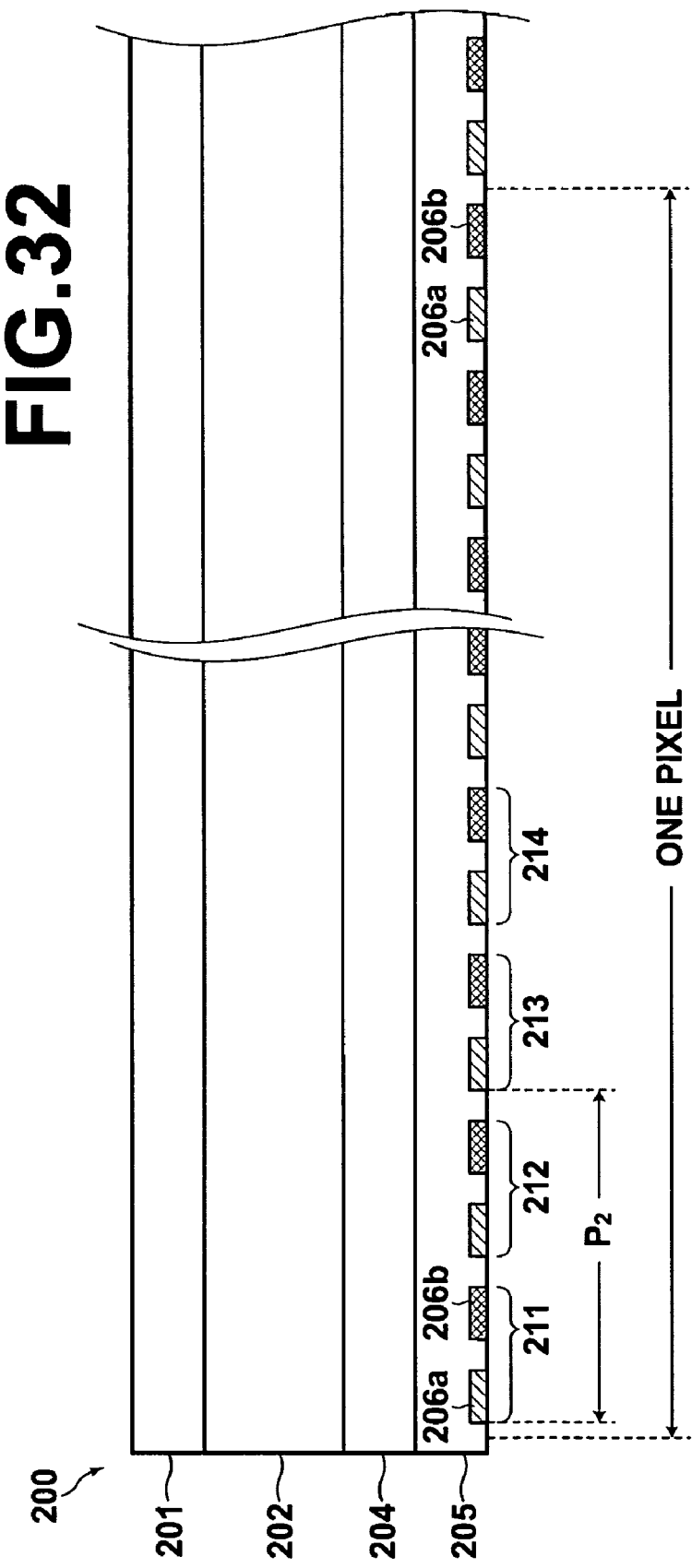

TOMOSYNTHESIS RADIOGRAPHING APPARATUS

CROSS-REFERENCE TO RELATED APPLICATIONS

The present application claims priority from Japanese Patent Application No. 2008-250276, filed Sep. 29, 2008, the contents of which are herein incorporated by reference in their entirety.

BACKGROUND OF THE INVENTION

1. Field of the Invention

The present invention relates to a tomosynthesis radiographing apparatus for radiographing a tomographic image of a subject.

2. Description of the Related Art

The use of a Talbot interferometer, which produces Talbot effect by a diffraction grating and generates Moire fringes in combination with another diffraction grating, in X-ray applications has been studied as described, for example, in U.S. Pat. No. 5,812,629 (Patent Document 1) and U.S. Pat. No. 7,180,979 (Patent Document 2).

Patent Document 1 or Patent Document 2 proposes an X-ray radiographing apparatus having an X-ray source, two diffraction gratings, and an X-ray image detector, in which the two diffraction gratings and X-ray image detector are formed on a planar substrate.

Where parallel beam, such as synchrotron radiation is used, the planar shape described above does not pose any problems, but it gives rise to a problem in medical diagnostic applications and the like in which an X-ray source that radiates widely spreading beams is generally used. That is, X-rays pass through the diffraction gratings at a center portion without any difficulty, but at a portion other than the center portion, X-rays are blocked by diffraction members and unable to pass through the diffraction gratings because the X-rays are incident from oblique directions. For example, Japanese Unexamined Patent Publication No. 2006-259264 (Patent Document 3) proposes an amplitude diffraction grating in which metal X-ray absorption members, each having a width of 2 to 10 µm and a thickness of 25 to 100 µm, are disposed at an equal interval of 2 to 10 µm. It can be thought that the use of such a diffraction grating may possibly cause the problem described above. Accordingly, large-size X-ray phase imaging has been difficult in medical diagnostic applications.

Consequently, Japanese Unexamined Patent Publication No. 2007-206075 (Patent Document 4) proposes an X-ray radiographing apparatus in which a diffraction grating strip is formed so as not to shade the optical path of a beam.

Further, Japanese Unexamined Patent Publication No. 2007-203063 (Patent Document 5) describes an X-ray radiographing apparatus having a detection element formed of multiple of elongated detection strips disposed parallel to the grid line of a phase diffraction grating. According to the X-ray radiographing apparatus, a single measurement with each beam allows a phase image to be obtained, reducing the number of required measurements. Still further, Japanese Unexamined Patent Publication No. 2007-203062 (Patent Document 6) proposes an x-ray radiographing apparatus for obtaining a phase image, as in Patent Document 5, and has a scintillation strip.

In the mean time, a radiographing apparatus having an X-ray emission unit in which multiple of X-ray sources are spatially distributed is proposed as described, for example, in U.S. Patent Application Publication No. 20070133747 (Patent Document 7) or U.S. Patent Application Publication No. 20070009088 (Patent Document 8). The apparatus allows X-ray imaging in which the influence of scattered X-rays are eliminated by combining images obtained by emitting X-rays outputted from each X-ray source.

Here, for example, if the distributed X-ray sources described in Patent Documents 7 and 8 are applied to one of the X-ray radiographing apparatuses described in Patent documents 1 to 6, the exposure range of a beam outputted from each X-ray source can be reduced, whereby the problem that a beam can not pass through a diffraction grating at a peripheral portion thereof may be avoided.

Use of an X-ray source that emits, for example, a pencil beam as the X-ray source that emits the narrow beam described above, however, multiple X-ray sources are required, when performing large size radiation phase imaging, according to the size, resulting in very low utilization efficiency of the X-ray sources. Further, provision of such a large number of X-ray sources results in a huge amount of heat which requires a large-scale structure for cooling the X-ray sources, leading to a cost increase.

In view of the circumstances described above, it is an object of the present invention to provide a tomosynthesis radiographing apparatus capable of eliminating the influence of scattered radiation and improving the utilization efficiency of a radiation source.

SUMMARY OF THE INVENTION

A tomosynthesis radiographing apparatus of the present is an apparatus including:

a radiation emission unit having multiple radiation sources for emitting radiation onto a subject, the radiation sources being distributed such that radiation emitted from each radiation source and transmitted through the subject forms a part of a projected image of the subject;

a radiation image detector for detecting radiation emitted from each radiation source of the radiation emission unit; and a tomographic image generation unit for generating a tomographic image of the subject based on detection information detected by the radiation image detector when radiation is irradiated onto the subject from different positions by the radiation emission unit, wherein each radiation source emits fan beam radiation and is disposed such that a plane of the fan beam having a wider spread angle intersects with an arrangement direction of the multiple radiation sources and is arranged parallel to each other.

In the tomosynthesis radiographing apparatus of the present invention, the spread angle of the fan beam in the plane having a wider spread angle may be ten times or more of a spread angle of the fan beam in a direction orthogonal to the plane.

Further, the radiation emission unit may be a unit constituted by the multiple radiation sources disposed in a line, the apparatus may further includes a shifting mechanism for shifting the radiation emission unit along a plane opposite to a detection surface of the radiation image detector, and the tomographic image generation unit may be a unit that generates a tomographic image of the subject based on detection information detected by the radiation image detector when the radiation emission unit is shifted by the shifting mechanism and radiation is irradiated onto the subject from different positions.

Still further, the radiation emission unit may be a unit constituted by the multiple radiation sources disposed in a line and the shifting mechanism may be a mechanism that shifts the radiation emission unit in a direction orthogonal to the line.

Further, the radiation emission unit may be a unit constituted by the multiple radiation sources disposed two-dimensionally, and radiation may be irradiated onto the subject from different positions by sequentially switching the radiation sources.

Still further, the apparatus may further include a first diffraction grating configured to be exposed to radiation emitted from the multiple radiation sources of the radiation emission unit and to produce Talbot interference or Talbot-Lau interference by the exposure and a second diffraction grating for diffracting radiation diffracted by the first diffraction grating, in which the first diffraction grating is disposed such that an extension direction of a diffraction member constituting the first diffraction grating corresponds to a spreading direction of the fan beam in the plane having a wider spread angle and the second diffraction grating is disposed such that an extension direction of a diffraction member constituting the second diffraction grating corresponds to the spreading direction of the fan beam in the plane having a wider spread angle, and the radiation image detector may be a detector that detects radiation diffracted by the second diffraction grating.

Further, the multiple radiation sources and the first diffraction grating may be disposed such that spacing between the multiple radiation sources in a direction orthogonal to the extension direction of the diffraction member of the first diffraction grating is smaller than a distance from the radiation sources to the first diffraction grating, and each of the multiple radiation sources may be a source that emits radiation such that exposure ranges of adjacent radiation sources at a position of the subject overlap with each other without any space between them and at an angle that substantially does not influence a diffraction property of the first diffraction grating in a peripheral portion of an exposure range at a position of the first diffraction grating.

Still further, the apparatus may further include a diffraction grating configured to be exposed to radiation emitted from the multiple radiation sources of the radiation emission unit and to produce Talbot interference or Talbot-Lau interference by the exposure, the radiation image detector may be a periodic information imaging radiation image detector for detecting periodic information of radiation diffracted by the diffraction grating, and the diffraction grating may be disposed such that an extension direction of a diffraction member constituting the diffraction grating corresponds to a spreading direction of the fan beam in the plane having a wider spread angle and the periodic information imaging radiation image detector may be disposed such that an extension direction of a periodicic structure member of the periodic information imaging radiation image detector corresponds to the spreading direction of the fan beam in the plane having a wider spread angle.

Further, the multiple radiation sources and the diffraction grating may be disposed such that spacing between the multiple radiation sources in a direction orthogonal to the extension direction of the diffraction member of the diffraction grating is smaller than a distance from the radiation sources to the diffraction grating, and each of the multiple radiation sources may be a source that emits radiation such that exposure ranges of adjacent radiation sources at a position of the subject overlap with each other without any space between them and at an angle that substantially does not influence a diffraction property of the diffraction grating in a peripheral portion of an exposure range at a position of the diffraction grating.

Still further, the radiation emission unit may be a unit that sequentially switches between certain radiation source groups and radiation source groups other than the certain radiation source groups of the multiple radiation sources disposed in a direction orthogonal to the plane of the fan beam having a wider spread angle to emit radiation from each radiation source group, and radiation sources belonging to each radiation source group may emit radiation such that exposure ranges of radiation emitted simultaneously from the radiation sources are separated from each other at a position of the radiation image detector.

According to the radiation tomosynthesis apparatus of the present invention, the apparatus uses a radiation emission unit having multiple radiation sources for emitting radiation onto a subject, which are distributed such that radiation emitted from each radiation source and transmitted through the subject forms a part of a projected image of the subject, and each radiation source emits fan beam radiation, and is disposed such that a plane of the fan beam having a wider spread angle intersects with an arrangement direction of the multiple radiation sources and is arranged parallel to each other. This may eliminate the influence of scattered radiation and improve the utilization efficiency of the radiation sources.

If the radiation emission unit is a unit constituted by the multiple radiation sources disposed in a line, the apparatus further includes a shifting mechanism for shifting the radiation emission unit along a plane opposite to a detection surface of the radiation image detector, and the tomographic image generation unit is a unit that generates a tomographic image of the subject based on detection information detected by the radiation image detector when the radiation emission unit is shifted by the shifting mechanism and radiation is irradiated onto the subject from different positions, the utilization efficiency of the radiation sources may further improved, and the amount of heat from the radiation sources may be reduced.

If the radiation emission unit is a unit constituted by the multiple radiation sources disposed two-dimensionally, and radiation is irradiated onto the subject from different positions by sequentially switching the radiation sources, detection information for generating a tomographic image may be obtained by a simple structure without requiring a shifting mechanism and the like.

If a first diffraction grating configured to be exposed to radiation emitted from the multiple radiation sources of the radiation emission unit and to produce Talbot interference or Talbot-Lau interference by the exposure and a second diffraction grating for diffracting radiation diffracted by the first diffraction grating are further provided, in which the first diffraction grating is disposed such that an extension direction of a diffraction member constituting the first diffraction grating corresponds to a spreading direction of the fan beam in the plane having a wider spread angle and the second diffraction grating is disposed such that an extension direction of a diffraction member constituting the second diffraction grating corresponds to the spreading direction of the fan beam in the plane having a wider spread angle, the utilization efficiency of the radiation sources may be improved and the beams may be prevented from being blocked at a peripheral portion of the diffraction gratings.

If the multiple radiation sources and the first diffraction grating are disposed such that spacing between the multiple radiation sources in a direction orthogonal to the extension direction of the diffraction member of the first diffraction grating is smaller than a distance from the radiation sources to the first diffraction grating, and each of the multiple radiation sources is a source that emits radiation such that exposure ranges of adjacent radiation sources at a position of the subject overlap with each other without any space between them and at an angle that substantially does not influence a diffraction property of the first diffraction grating in a peripheral portion of an exposure range at a position of the first diffraction grating, an appropriate phase image without any space may be obtained.

If a diffraction grating configured to be exposed to radiation emitted from the multiple radiation sources of the radiation emission unit and to produce Talbot interference or Talbot-Lau interference by the exposure is further provided and a periodic information imaging radiation image detector for detecting periodic information of radiation diffracted by the diffraction grating is used as the radiation image detector, in which the diffraction grating is disposed such that an extension direction of a diffraction member constituting the diffraction grating corresponds to a spreading direction of the fan beam in the plane having a wider spread angle and the periodic information imaging radiation image detector is disposed such that an extension direction of a periodicic structure member of the periodic information imaging radiation image detector corresponds to the spreading direction of the fan beam in the plane having a wider spread angle, the utilization efficiency of the radiation sources may be improved and the beams may be prevented from being blocked at a peripheral portion of the diffraction grating or the periodic information imaging radiation image detector.

If the multiple radiation sources and the diffraction grating are disposed such that spacing between the multiple radiation sources in a direction orthogonal to the extension direction of the diffraction member of the diffraction grating is smaller than a distance from the radiation sources to the diffraction grating, and each of the multiple radiation sources is a source that emits radiation such that exposure ranges of adjacent radiation sources at a position of the subject overlap with each other without any space between them and at an angle that substantially does not influence a diffraction property of the diffraction grating in a peripheral portion of an exposure range at a position of the diffraction grating, an appropriate phase image without any space may be obtained.

If the radiation emission unit is a unit that sequentially switches between certain radiation source groups and radiation source groups other than the certain radiation source groups of the multiple radiation sources disposed in a direction orthogonal to the plane of the fan beam having a wider spread angle to emit radiation from each radiation source group, and radiation sources belonging to each radiation source group emit radiation such that exposure ranges of radiation emitted simultaneously from the radiation sources are separated from each other at a position of the radiation image detector, the influence of scattered radiation may be reduced by detecting only straightly propagated component of radiation emitted from the radiation sources.

BRIEF DESCRIPTION OF THE DRAWINGS

FIG. 31A is a sectional view of a periodic information imaging radiation image detector in a fourth embodiment of the tomosynthesis radiographing apparatus of the present invention.

FIG. 31B is an X-Z sectional view of the periodic information imaging radiation image detector shown in FIG. 31A.

FIG. 31C is an X-Y sectional view of the periodic information imaging radiation image detector shown in FIG. 31A.

FIG. 32 illustrates a configuration of linear electrodes of periodic information imaging radiation image detector in the tomosynthesis radiographing apparatus according to the fourth embodiment.

DESCRIPTION OF THE PREFERRED EMBODIMENTS

Figure 1:
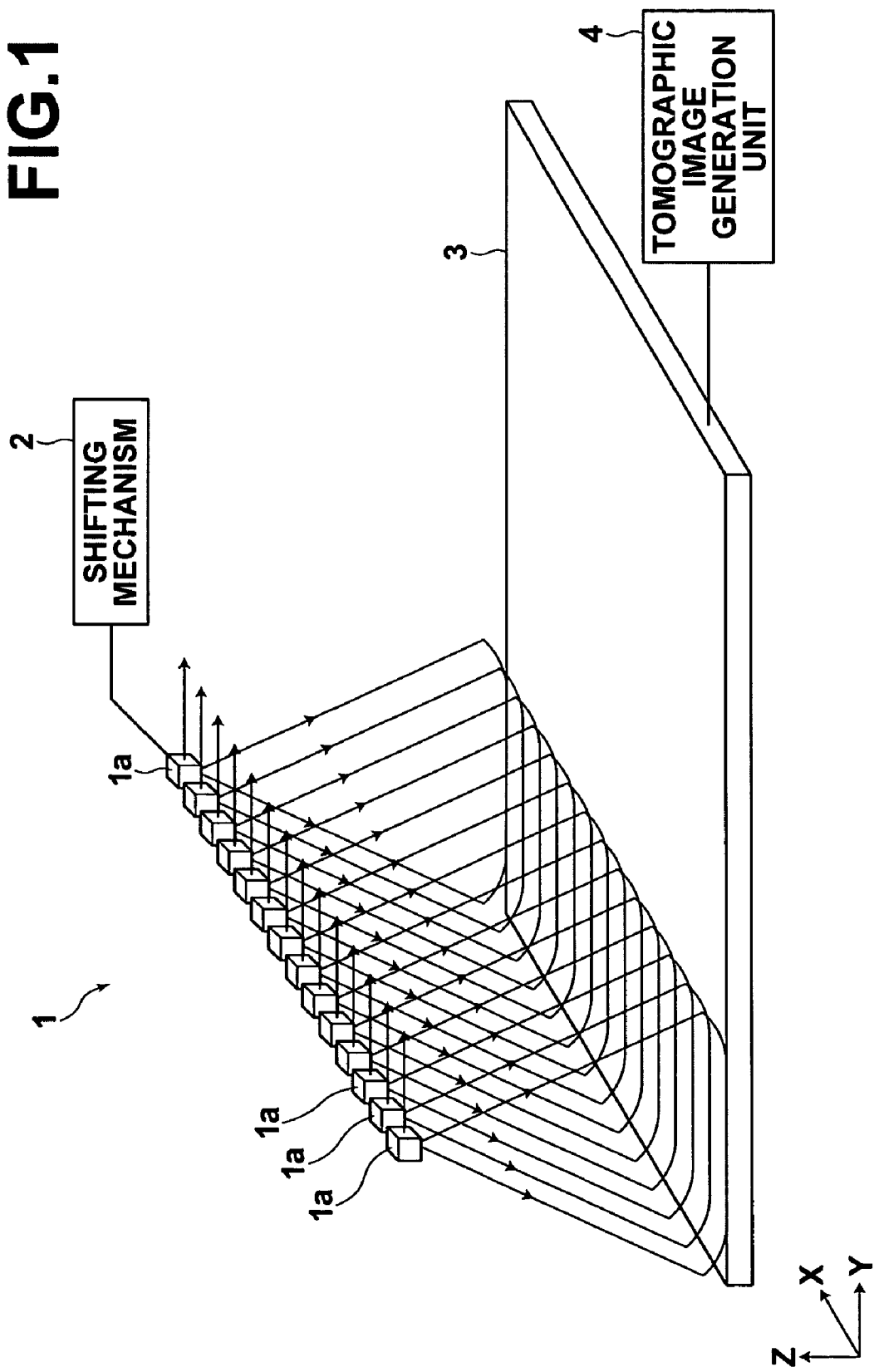
FIG. 1 is a schematic construction diagram of a first embodiment of the tomosynthesis radiographing apparatus of the present invention.
Figure 2:
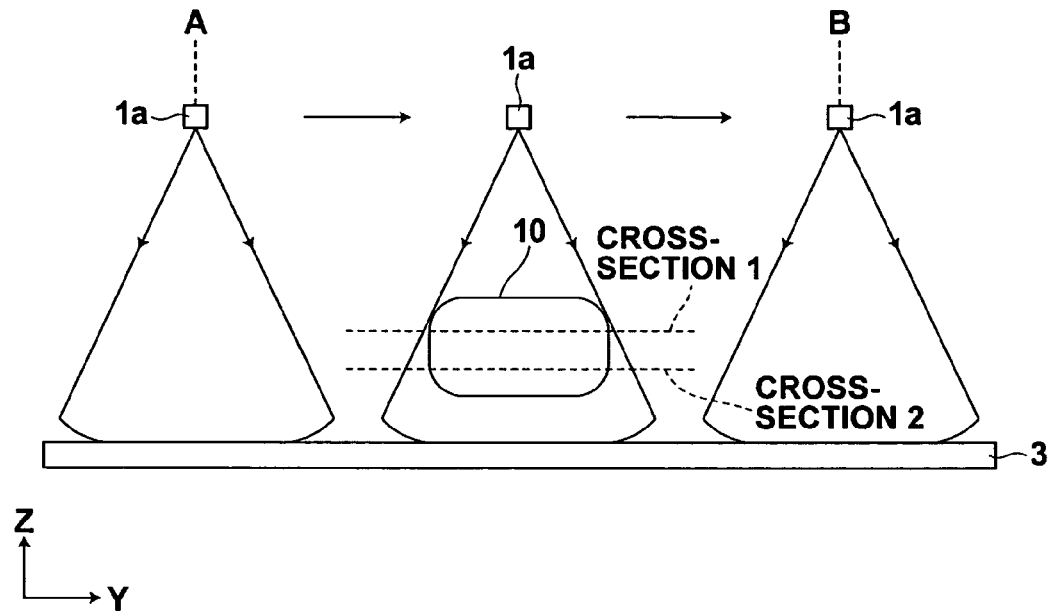
FIG. 2 is a Z-Y sectional view of the tomosynthesis radiographing apparatus shown in FIG. 1.

Hereinafter, a first embodiment of the tomosynthesis radiographing apparatus of the present invention will be described with reference to the accompanying drawings. FIG. 1 is a perspective view of the tomosynthesis radiographing apparatus according to the first embodiment. FIG. 2 is a side view (Z-Y sectional view) of the tomosynthesis radiographing apparatus shown in FIG. 1. The thickness direction in FIG. 2 corresponds to X direction in FIG. 1.

As shown in FIGS. 1 and 2, the tomosynthesis radiographing apparatus includes radiation emission unit 1 that emits radiation onto subject 10, shifting mechanism 2 that shifts radiation emission unit 1 in Y direction in FIG. 1, radiation image detector 3 that detects radiation emitted from radiation emission unit 1 and transmitted through subject 10, and tomographic image generation unit 4 that generates a tomographic image of subject 10 based on detection information detected by radiation image detector 3 when radiation is irradiated onto subject 10 from different positions.

As shown in FIG. 1, radiation emission unit 1 includes multiple radiation sources 1a for emitting radiation disposed in a line in X direction along a plane opposite to the detection surface of radiation image detector 3.

Radiation emitted from each radiation source 1a is detected by radiation image detector 3 after transmitting through a subject. Each radiation source 1a is distributed such that the radiation emitted from each radiation source 1a and transmitted through the subject forms a part of a projected image of the subject.

Radiation emission unit 1 is shifted from position A to position B illustrated in FIG. 2 by shifting mechanism 2, and partial projected images formed by radiation emitted from each radiation source 1a are combined to form a part or a complete projected image.

Each radiation source 1a emits a fan beam, and is disposed such that a plane in which the fan beam has a wider spread angle intersects with the arrangement direction of radiation sources 1a (X direction in FIG. 1) and parallel to each other. That is, each radiation source 1a outputs a fan beam having a wider spread angle in Y direction than in X direction in FIG. 1.

Figure 3A:
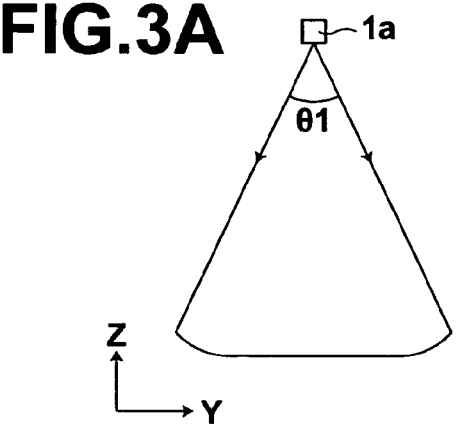
FIG. 3A illustrates a plane in which a fan beam emitted from a radiation source has a wider spread angle.
Figure 3B:
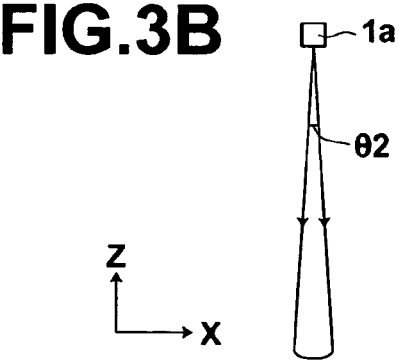
FIG. 3B illustrates a plane in which a fan beam emitted from a radiation source has a narrower spread angle.

The spread angle of the fan beam outputted from each radiation source 1a in the plane having a wider spread angle is not less than ten times as large as a spread angle of the fan beam in the direction orthogonal to the plane. That is, as illustrated in FIGS. 3A and 3B, it is desirable that spread angle θ1 of a fan beam outputted from each radiation source in Y direction be not less than ten times as large as spread angle θ2 in X direction.

Figure 4:
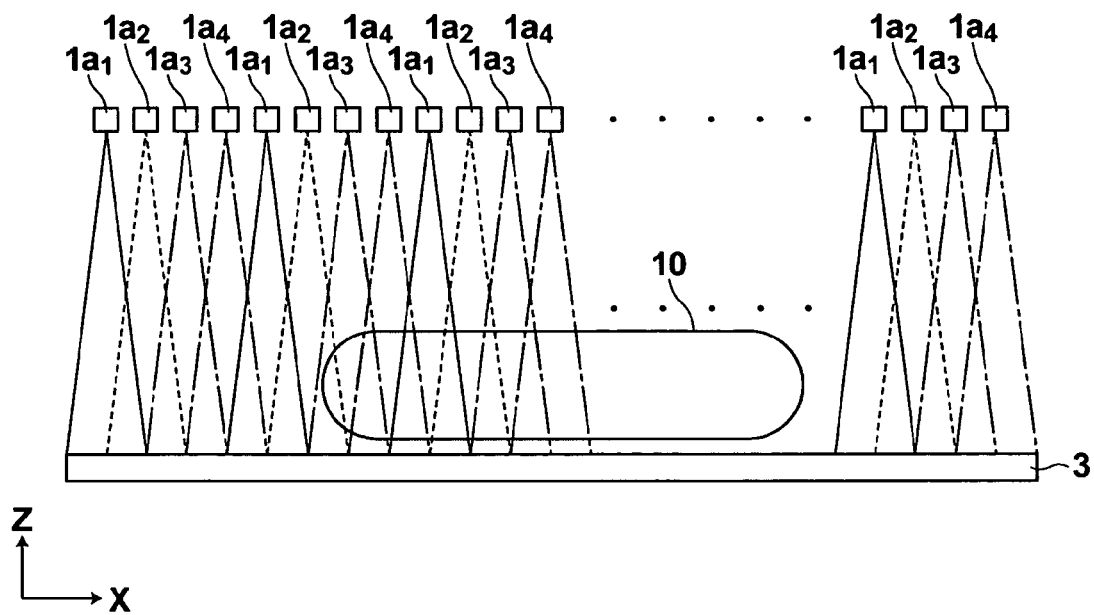
FIG. 4 illustrates the exposure range of a fan beam outputted from each radiation source.

Further, it is desirable that exposure ranges of fan beams outputted from adjacent radiation sources overlap with each other on subject 10 as illustrated in FIG. 4. If that is the case, for example, adjacent radiation sources 1a1, 1a2, 1a3, and 1a4 can be sequentially switched to emit a fan beam. That is, any structure may be employed as long as exposure ranges of fan beams outputted from radiation sources at the same time are sufficiently separated from each other on radiation image detector 3 and exposure ranges of fan beams outputted from all radiation sources are arranged without any space between them on the subject.

Specific examples of radiation source 1a include an X-ray source having a cold cathode electron source, a plasma X-ray source, and an X-ray source using an electron accelerator, as well as an X-ray source using an ordinary hot cathode electron source.

In the present invention, the radiation emission unit 1 may have a structure other than that described above, which will be described later.

Radiation image detectors used in conventional radiographing apparatuses, such as direct conversion or indirect conversion flat panel detectors, imaging plates, intensifying screen-film combinations, and the like, can be used as radiation image detector 3. Therefore, radiation image detector 3 will not be elaborated upon further here.

Tomographic image generation unit 4 generates a tomographic image of a subject based on an image signal representing multiple radiation images sequentially detected by radiation image detector 3 in association with the shift of radiation emission unit 1. Tomographic image generation unit 4 may use a so-called shift-and-add method in which a tomographic image is generated by shifting image signals, representing multiple radiation images obtained by emitting radiation onto subject 10 from different positions by radiation emission unit 1, according to a desired cross-sectional position of the subject and adding the signals. By controlling the shift amount of each image signal, a tomographic image corresponding to cross-section 1 or cross-section 2 shown in FIG. 2 may be generated.

An operation of the tomosynthesis radiographing apparatus of the present invention will be described.

First, subject 10 is placed between radiation emission unit 1 and radiation image detector 3, as shown in FIG. 2. Then, radiation emission unit 1 is shifted in Y direction by shifting mechanism 2 and radiation is emitted from each radiation source 1a of radiation emission unit 1 onto radiation image detector and subject 10 at the same time.

Radiation images are sequentially detected by radiation image detector 3 as radiation emission unit 1 is shifted, and an image signal representing each radiation image is outputted to tomographic image generation unit 4.

Then, tomographic image generation unit 4 performs shift processing on image signals representing multiple radiation images obtained when radiation emission unit 1 is shifted from position A to position B according to a desired cross-sectional position of the subject and generates a tomographic image according to the cross-sectional position by adding the shift processed image signals.

In the tomosynthesis radiographing apparatus according to the first embodiment, radiation emission unit 1 is formed by arranging multiple radiation sources 1a in a line, but a plurality of lines of radiation sources may be provided in Y direction. In this case, it is desirable that radiation be emitted by sequentially switching the radiation sources such that exposure ranges of radiation simultaneously emitted from each radiation source are sufficiently separated from each other on radiation image detector 3.

Figure 5:
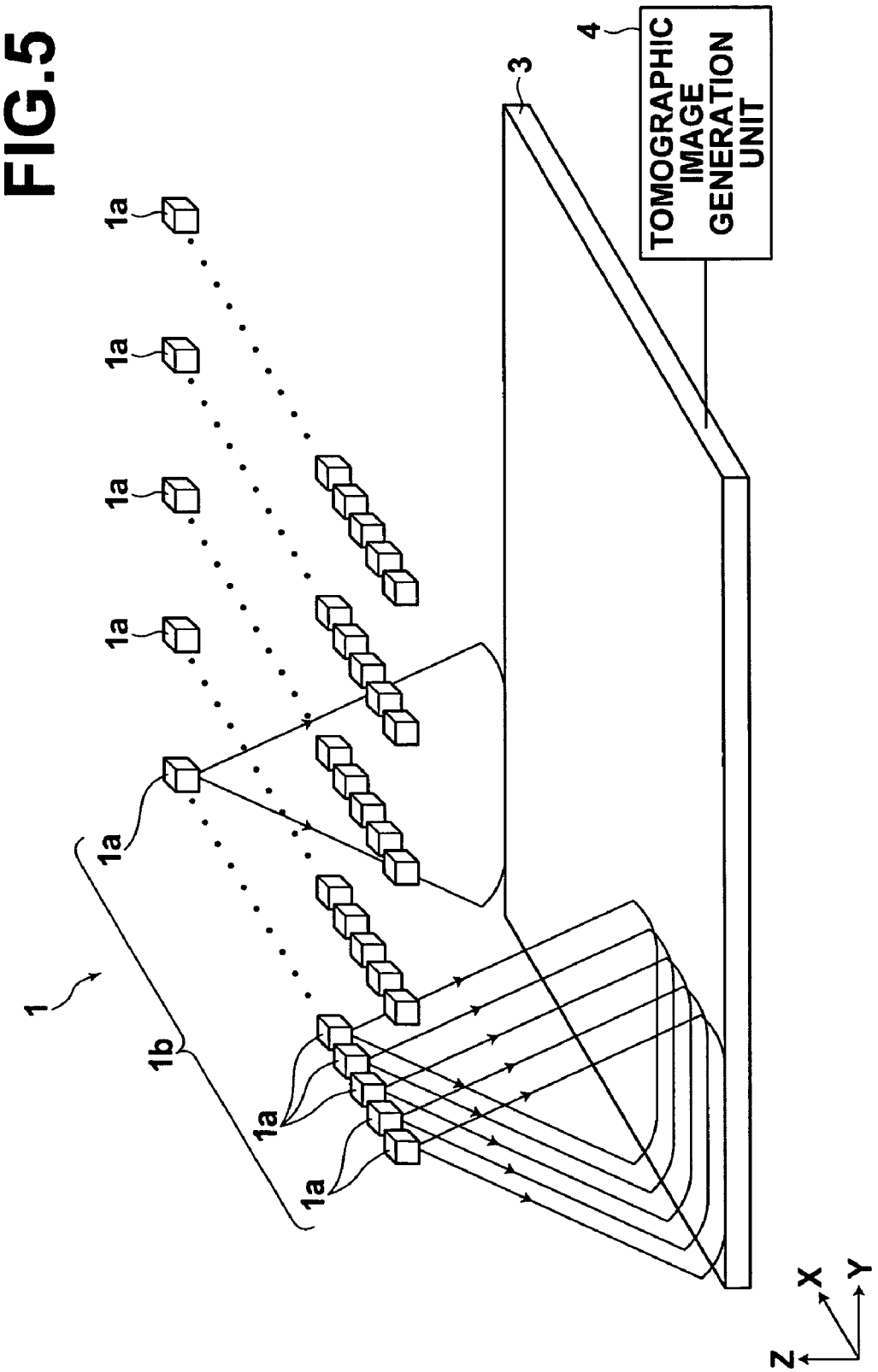
FIG. 5 illustrates a radiation emission unit in which radiation sources are disposed two-dimensionally.

Further, in the first embodiment, multiple radiation images for generating a tomographic image are obtained by shifting radiation emission unit 1 by shifting mechanism 2. But a configuration may be adopted, for example, in which radiation sources 1*a* are arranged two dimensionally along a plane opposite to the detection surface of radiation image detector 3 and rows 1*b* of radiation sources 1*a* are sequentially switched in Y direction to emit radiation onto the subject from different positions without providing a shifting mechanism, as shown in FIG. 5. The row of radiation sources 1*a* may be provided in a number sufficient for obtaining a tomographic image.

Figure 6:
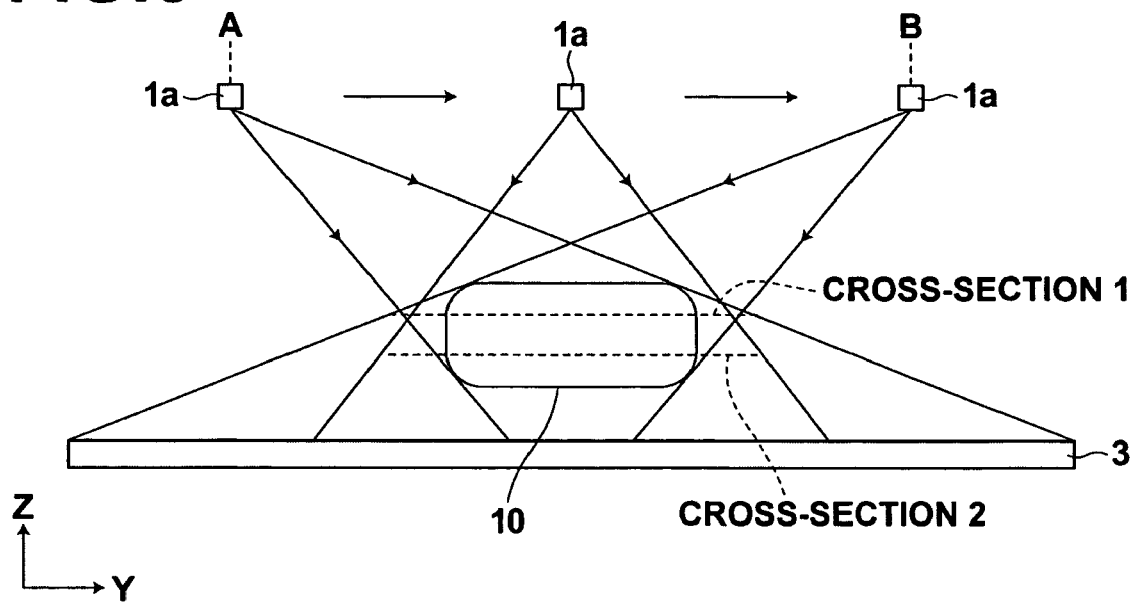
FIG. 6 illustrates an embodiment in which the emission direction of radiation outputted from a radiation source is changed.

In the tomosynthesis radiographing apparatus according to the first embodiment, the emission direction of radiation outputted from each radiation source 1*a* is fixed. But, the emission direction of radiation outputted from each radiation source 1*a* of radiation emission unit 1 may be changed so as to correspond to the direction toward the subject by changing the relative position between each radiation source and a collimator (not shown in FIG. 6) according to the position of radiation emission unit 1 between positions A and B, as shown in FIG. 6. By changing the emission direction in the manner as described above, the angle of radiation outputted from each radiation source 1*a* may be broadened and a tomographic image with a sharper focus on the cross-section than the first embodiment may be generated.

Figure 7:
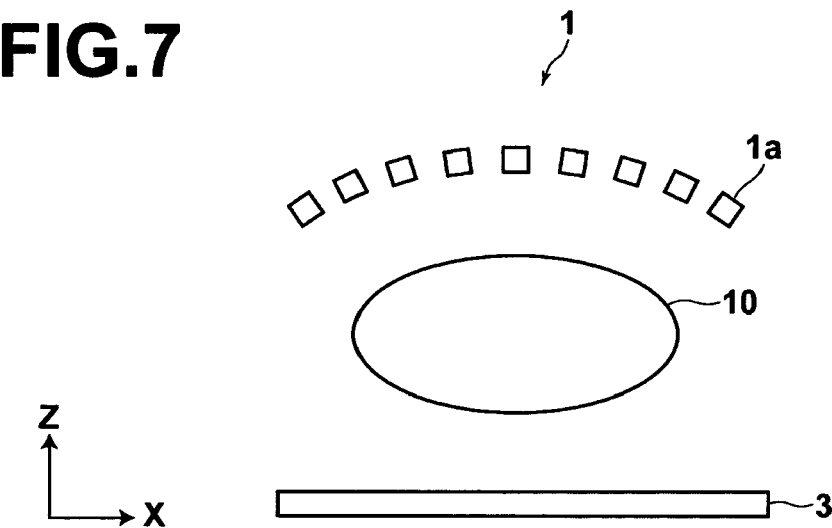
FIG. 7 illustrates another embodiment of the radiation emission unit.

Further, in the tomosynthesis radiographing apparatus according to the first embodiment, radiation sources 1*a* are disposed linearly in X direction, but they are not necessarily disposed linearly and, for example, they may be disposed in an arc shape on X-Z plane, as illustrated in FIG. 7.

Still further, in the tomosynthesis radiographing apparatus according to the first embodiment, radiation image detector 3 is disposed over the entire range in which radiation is emitted by shifting radiation emission unit 1. But, a radiation image detector having a size corresponding to the exposure range of radiation outputted from radiation emission unit 1 may be provided and the radiation image detector may be shifted in association with the shift of the radiation emission unit 1, thereby sequentially detecting radiation emitted from radiation emission unit 1 at each position by the radiation image detector.

Figure 8:
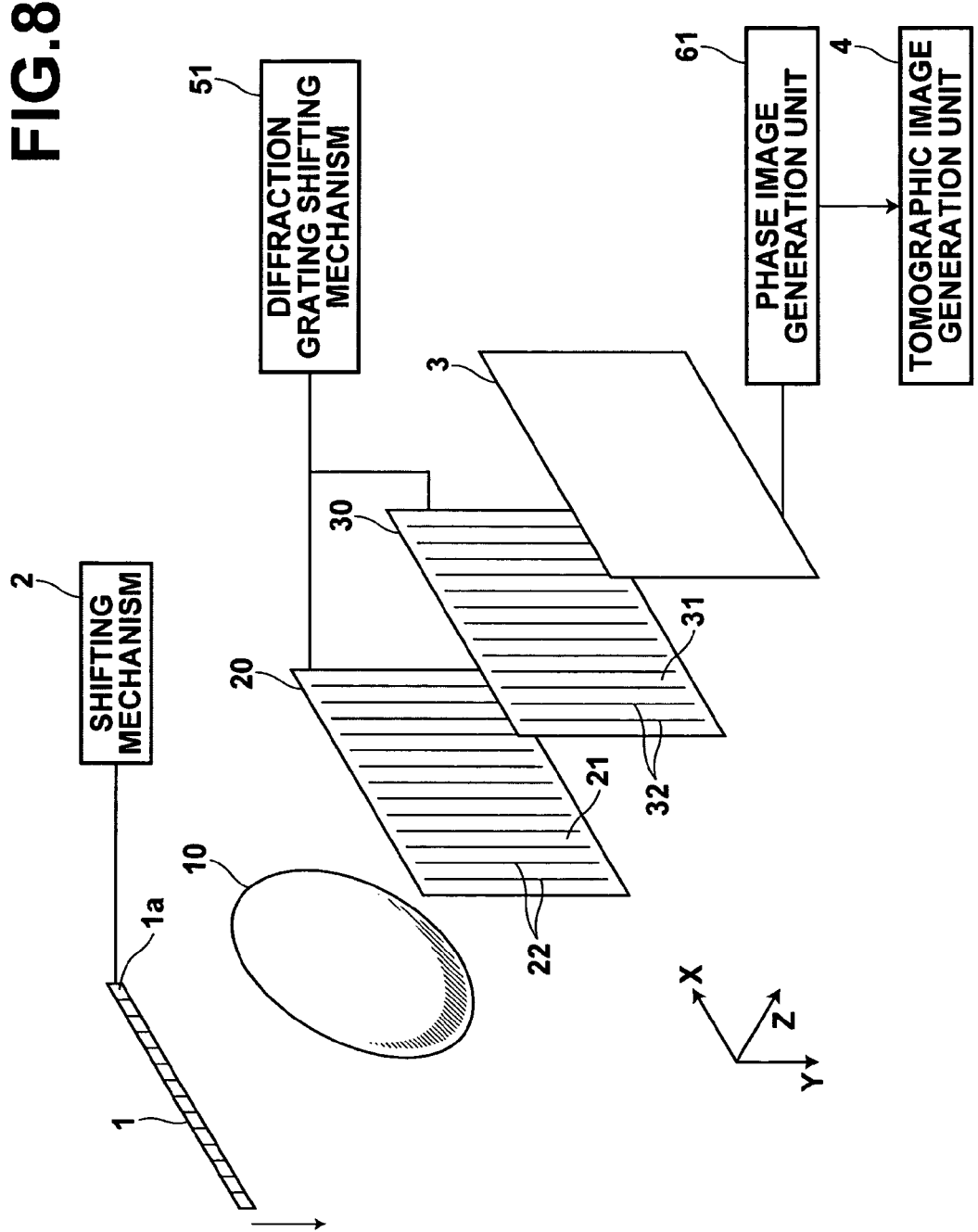
FIG. 8 is a schematic construction diagram of a second embodiment of the tomosynthesis radiographing apparatus of the present invention.
Figure 9:
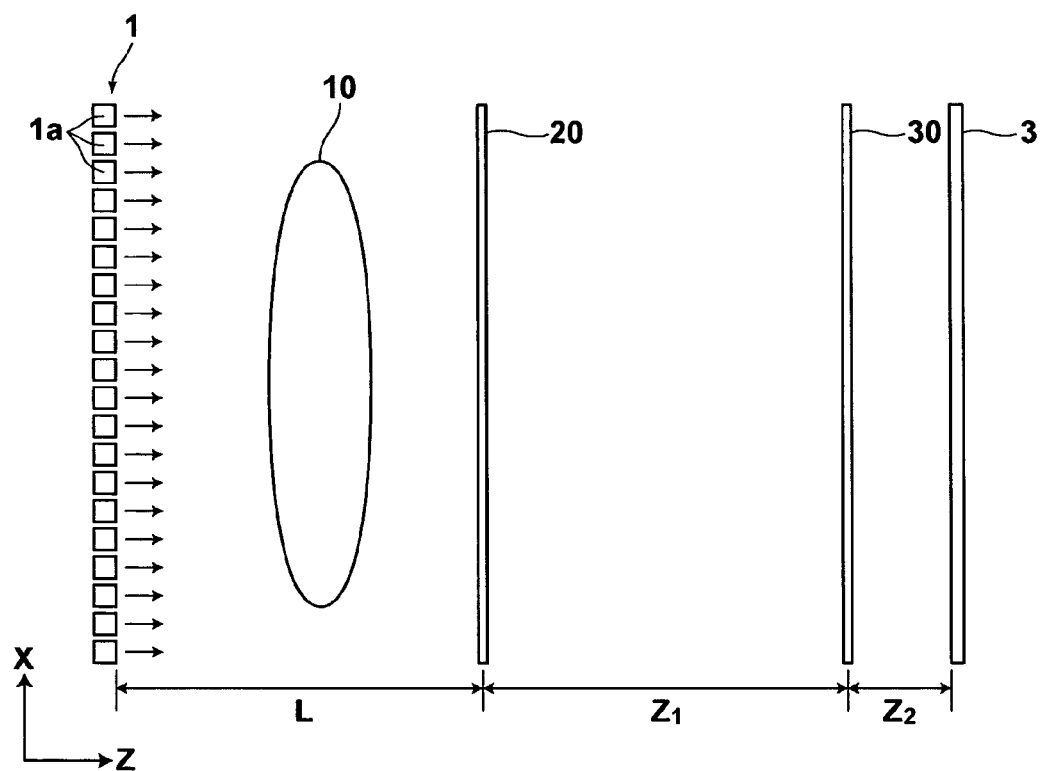
FIG. 9 is a top view of the tomosynthesis radiographing apparatus shown in FIG. 8.

Next, a second embodiment of the tomosynthesis radiographing apparatus of the present invention will be described. FIG. 8 is a perspective view of the tomosynthesis radiographing apparatus according to the second embodiment. FIG. 9 is a top view (X-Z sectional view) of the tomosynthesis radiographing apparatus shown in FIG. 8. The thickness direction in FIG. 9 corresponds to Y direction in FIG. 8.

As shown in FIGS. 8 and 9, the tomosynthesis radiographing apparatus of the second embodiment further includes a first diffraction grating 20 configured to be exposed to the radiation emitted from radiation emission unit 1 and to produce Talbot interference or Talbot-Lau interference by the exposure, second diffraction grating 30 for diffracting the radiation diffracted by first diffraction grating 20, diffraction grating shifting mechanism 51 for shifting first and second diffraction gratings 20, 30 in a direction orthogonal to diffraction members 20, 30 (X direction in FIG. 8) along respective planes, and phase image generation unit 61 for generating a phase image based on an image signal detected by radiation image detector 3, in addition to the tomosynthesis radiographing apparatus of the first embodiment.

As in the first embodiment, radiation emission unit 1 includes multiple radiation sources 1*a* for emitting radiation disposed in a line in X direction along a plane opposite to the detection surface of radiation image detector 3.

Each radiation source 1*a* of radiation emission unit 1 is a unit that emits a fan beam identical to that of the first embodiment. The radiation has sufficient spatial coherence to produce a Talbot effect when irradiated to first diffraction grating 20. In the first embodiment, an X-ray source having a cold cathode electron source, a plasma X-ray source, and an X-ray source using an electron accelerator, as well as an X-ray source using an ordinary hot cathode electron source, are cited as examples of radiation source 1*a* constituting radiation emission unit 1. In addition to this, the following conditions are added in the second embodiment. For example, radiation emission unit 16 may be formed of a cold cathode electron source 16*a* having multiple electron emission units 16*b* that emit electrons, metal target 16*c*, and multi-slit 16*d* made of a slit member and transmits radiation emitted from metal target 16*c*, as illustrated in FIG. 10.

As electron source 16*a*, for example, an electron source of an FED (Field Emission Display) or a SED (Surface-conduction Electron-Emitter Display) may be used.

The purpose of multi-slit 16*d* is to take out X-rays generated at specific locations from those emitted from metal target 16*c* by the collision of electrons emitted from each electron emission unit 16*b*. The multi-slit 16*d* is disposed such that the direction in which each slit extends corresponds to Y direction (thickness direction in FIG. 10). The interval of multi-slit 16*d* is determined based on a Talbot-Lau interference condition. In this way, radiation passed through a collimator (now shown) becomes identical to the fan beam outputted from each radiation source 1*a* in the first embodiment.

Figure 10:
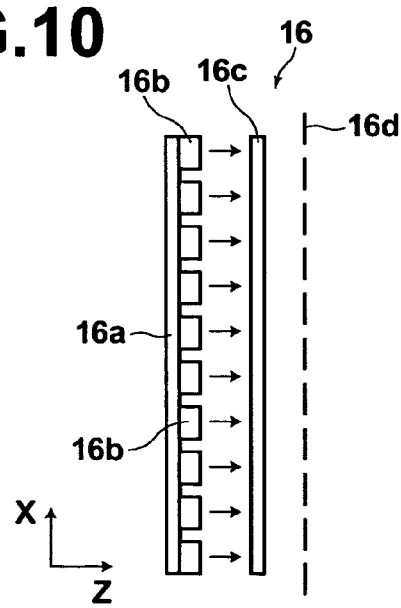
FIG. 10 illustrates another embodiment of the radiation emission unit.

In radiation emission unit 16 shown in FIG. 10, metal target 16*c* may be formed of metal wires disposed parallel to each other in Y direction (thickness direction in FIG. 10) without providing multi-slit 16*d*. The interval between the metal wires is determined based on a Talbot-Lau interference condition. In this case, radiation emitted from the metal wire becomes identical to the fan beam outputted from each radiation source 1*a* in the first embodiment.

Further, in radiation emission unit 16 shown in FIG. 10, cold cathode electron source 16*a* may be formed of linear cold cathode electron sources disposed in parallel stripes in Y direction (thickness direction in FIG. 10) without providing multi-slit 16*d*. The interval between the stripes is determined based on a Talbot-Lau interference condition. In this case, radiation emitted from metal target 16*c* by the collision of electrons emitted from each stripe shaped cold cathode electron source and passed through a collimator (now shown) becomes identical to the fan beam outputted from each radiation source 1*a* in the first embodiment.

Preferably, multiple radiation sources 1*a* of radiation emission unit 1 are those that emit radiation such that exposure ranges of adjacent radiation sources 1*a* at a position of subject 10 overlap with each other without any space between them and at an angle that substantially does not influence a diffraction property of first diffraction grating 20 in a peripheral portion of an exposure range at the position of first diffraction grating 20. Conditions of the angle will be described in detail later.

Figure 11:
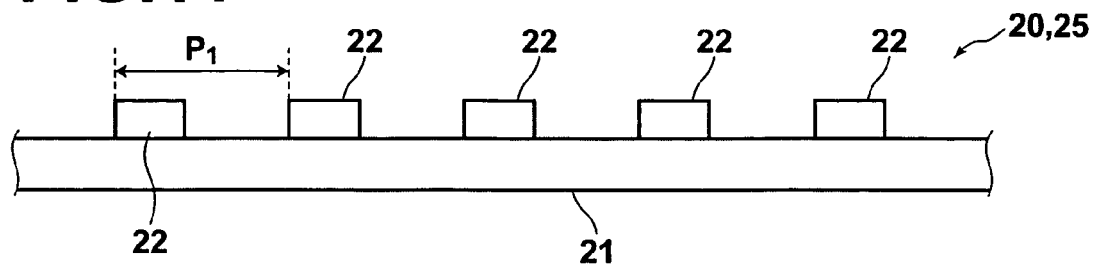
FIG. 11 is a diagram of a first diffraction grating, schematically illustrating a construction thereof.

First diffraction grating 20 is formed along a planar surface parallel to the detection surface of radiation image detector 3. As shown in FIG. 11, first diffraction grating 20 includes substrate 21 and a plurality of diffraction members 22 provided on substrate 21. Each of the plurality of diffraction members 22 is formed in a linear shape extending in one direction (thickness direction in FIG. 11). Spacing $P_1$ between each of the plurality of diffraction members 22 (the periodic of the diffraction grating) is constant in the present embodiment. As for the material of diffraction member 22, for example, gold may be used. Preferably, diffraction member 22 forms a so-called phase diffraction grating that phase modulates the irradiated radiation by about 80 to 100° (ideally, 90°. The thickness of gold required in the X-ray energy range of ordinary medical diagnosis is about one to several micrometers.

Figure 12:
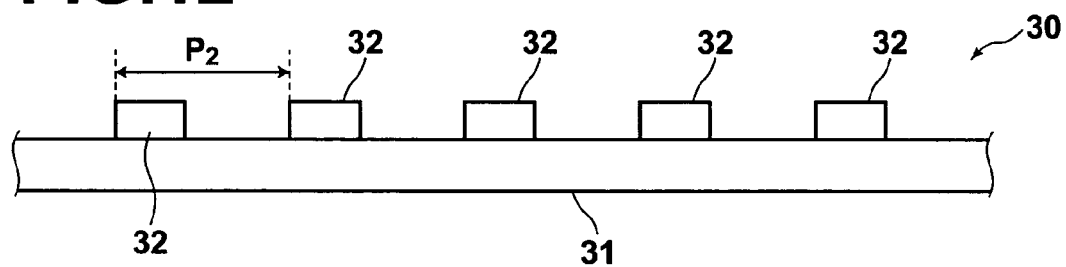
FIG. 12 is a diagram of a second diffraction grating, schematically illustrating a construction thereof.

Second diffraction grating 30 is formed along a planar surface parallel to the detection surface of radiation image detector 3. As shown in FIG. 12, second diffraction grating 30 includes substrate 31 and a plurality of diffraction members 32 provided on substrate 31, as in first diffraction grating 20. Each of the plurality of diffraction members 32 is formed in a linear shape extending in one direction (thickness direction in FIG. 12). Spacing $P_2$ between each of the plurality of diffraction members 32 (the periodic of the diffraction grating) is constant in the present embodiment. As for the material of diffraction member 32, for example, gold may be used. Second diffraction grating 30 is structured to form image contrast by diffracting the radiation diffracted by first diffraction grating 20. Preferably, second diffraction grating 30 is an amplitude diffraction grating having thicker diffraction members, but it may be constructed in the same manner as first diffraction grating 20. In order to make second diffraction grating 30 as an amplitude diffraction grating, the diffraction members need to sufficiently absorb radiation. The thickness of gold required in the X-ray energy range of ordinary medical diagnosis is around ten to several tens of micrometers.

The ratio between distance L from radiation source $1a$ to first diffraction grating 20 and pitch $P_1$ in first diffraction grating 20 may be set substantially equal to the ratio between distance from radiation source $1a$ to second diffraction grating 30, $L+Z1$, and pitch $P_2$ in second diffraction grating 30.

First diffraction grating 20 and second diffraction grating 30 are arranged such that the extension direction of diffraction members 22, 32 forming the gratings corresponds to a spreading direction of a fan beam outputted from each radiation source $1a$ in the plane having a wider spread angle. That is, first diffraction grating 20 and second diffraction grating 30 are arranged such that the extension direction of diffraction members 22, 32 forming the gratings corresponds to the shifting direction of radiation emission unit 1 (Y direction).

Radiation image detector 3 is identical to that of the first embodiment.

In the tomosynthesis radiographing apparatus according to the second embodiment, a Talbot interferometer is constructed with radiation source $1a$, first diffraction grating 20, and second diffraction grating 30. Conditions for the Talbot interferometer will be described hereinafter.

First, coherence length l is calculated in the following manner.

$$l = \frac{\lambda}{a/(L+Z_1+Z_2)} \quad (1)$$

where,
λ: wavelength of radiation (generally, center wavelength)
a: aperture diameter of radiation source $1a$ in a direction substantially orthogonal to diffraction members.

L: distance from radiation source $1a$ (if a slit is used in the radiation emission unit, from the position of the slit) to first diffraction grating 20 (FIG. 9)
$Z_1$: distance from first diffraction grating 20 to second diffraction grating 30 (FIG. 9)
$Z_2$: distance from second diffraction grating 30 to radiation image detector 3 (FIG. 9)

Distance $Z_1$ between first diffraction grating 20 and second diffraction grating 30 needs to substantially satisfy the following conditions, on the assumption that first diffraction grating 20 is a phase diffraction grating.

$$Z_1 = \left(m + \frac{1}{2}\right)\frac{P_1^2}{\lambda} \quad (2)$$

where, m is an integer, $P_1$ is the periodic of the diffraction members described above.

$$Z_1 = (m+1)\frac{P_1^2}{\lambda} \quad (3)$$

where, m is 0 or a positive integer, and λ is the wavelength of radiation.

As described above, shifting mechanism 51 is a mechanism for shifting first and second diffraction gratings 20, 30 in X direction. For example, first and second diffraction gratings 20, 30 may be shifted by 1/n (n is an integer not less than two) of pitch $P_1$ of the first diffraction members and take a radiation image at each position, whereby image signals of n-types of phase components may be obtained. It is preferable, for example, to shift first and second diffraction gratings 20, 30 such that image signals corresponding to four or six types of phase components are obtained.

An operation of tomosynthesis radiographing apparatus of the present embodiment will now be described.

First, as illustrated in FIG. 8, subject 10 is placed between radiation emission unit 1 and first diffraction grating 20. Then, radiation is emitted from each radiation source $1a$ of radiation emission unit 1 at the same time onto first diffraction grating 20. The radiation irradiated to first diffraction grating 20 passes through first diffraction grating 20. At this time, a Talbot effect is produced in first diffraction grating 20.

The Talbot effect as used herein refers to that, when a plane wave passes through a phase diffraction grating, a self-image of the diffraction grating is formed at the distance given by Formula (2) above. In the case described above, the radiation is phase shifted by subject 10, so that the wave front of the radiation incident on first diffraction grating 20 is distorted. Accordingly, the self-image of first diffraction grating 20 is deformed according to the distortion. Then, the radiation passes through second diffraction grating 30. As a result, the deformed self-image of first diffraction grating 20 and second diffraction grating 30 are superimposed with each other, whereby image contrast may be generated in the radiation. The image contrast generally takes the form of Moire fringes and can be detected by radiation image detector 3. The generated Moire fringes are modulated by subject 10. The amount of modulation is proportional to the angle by which the radiation is bent due to the refraction effect of subject 10. Therefore, subject 10 and an internal structure of the subject may be detected by analyzing the Moire fringes detected by radiation image detector 3.

Then, an image signal corresponding to a phase component when first and second diffraction gratings 20, 30 are placed at a predetermined position in the manner as described above is detected by radiation image detector 3. Then, first and second diffraction gratings 20, 30 are shifted by shifting mechanism 51 in X direction by 1/n (n is an integer not less than two) of pitch $P_1$ of the first diffraction members, and an image signal corresponding to the phase component at each position is detected by radiation image detector 3.

Image signals detected in the manner as described above are inputted to phase image generation unit 61. Then, phase image generation unit 61 generates a partial phase image with respect to each detection range of radiation image detector 3 based on image signals of a plurality of phase components detected by radiation image detector 3 in each detection range corresponding to the exposure range of radiation emitted from each radiation source 1a. That is, a partial phase image corresponding to each radiation source 1a is generated. Thereafter, the partial phase images are combined to produce a complete phase image. The method for generating a complete phase image is not limited to this. For example, a complete phase image may be generated by generating an image signal corresponding to entire phase components based on an image signal of each phase component detected by each detection range of radiation image detector 3 and a phase image may be generated based on the image signal of entire phase components.

Then, radiation emission unit 1 is shifted in Y direction, as in the first embodiment; and at each predetermined position, radiation is emitted from each radiation source 1a of radiation emission unit 1 and first and second diffraction gratings 20, 30 are shifted, whereby a phase image at each position of radiation emission unit 1 is sequentially generated.

Image signals representing a plurality of phase images generated in phase image generation unit 65 are inputted to tomographic image generation unit 4. Tomographic image generation unit 4 performs shift processing on the inputted plurality of image signals according to a desired cross-sectional position of the subject and generates a tomographic image according to the cross-sectional position by adding the shift processed image signals, as in the first embodiment.

Here, as described above, it is preferable that each radiation source 1a emits radiation such that the exposure range at the position of subject 10 is arranged without any space and at an angle that substantially does not influence a diffraction property of first diffraction grating 20 and second diffraction grating 30 at peripheral portions of the exposure ranges at the positions of first diffraction grating 20 and second diffraction grating 30. Hereinafter, the angle will be discussed. Here, the allowable range of the angle will be discussed in terms of the positional displacement of first diffraction grating 20.

Figure 13:
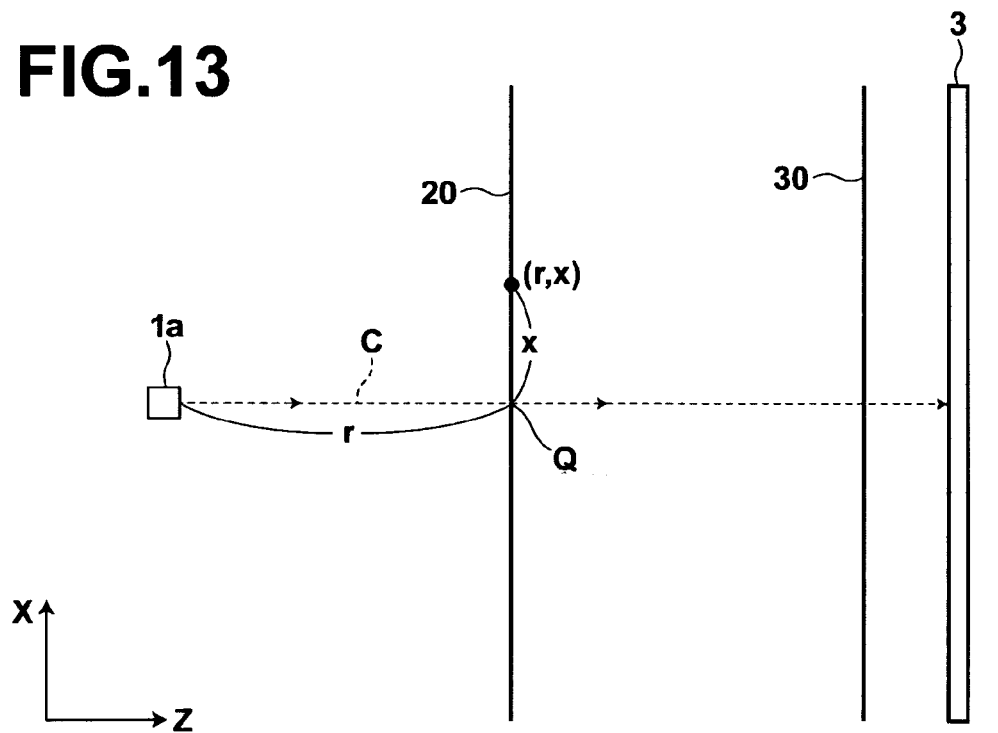
FIG. 13 illustrates conditions of spread angle of radiation emitted from a radiation source.

Assuming a required pitch of diffraction members at a position (r, x) away from intersection point Q between central axis C of the radiation emitted from radiation source 1a and first diffraction grating 20 by distance x in a direction orthogonal to the diffraction members to be $\Delta x$, $\Delta x$ can be represented by Formula (4) below (FIG. 13, which is a top view of the tomosynthesis radiographing apparatus shown in FIG. 8. The thickness direction in FIG. 13 corresponds to Y direction in FIG. 8.)

$$\Delta x = r\Delta\theta \times \frac{\tan\theta}{\theta} \times \left\{\sqrt{(r^2 + x^2)} \times \frac{1}{r}\right\} \times \frac{1}{\cos\theta} \tag{4}$$

where, r is the distance from radiation source 1a (if a slit is used in the radiation emission unit, to be described later, from the position of the slit) to first diffraction grating 20, and $r\Delta\theta$ is the pitch of the diffraction members at intersection point Q between the central axis C of the radiation beam and first diffraction grating 20.

Here, $x/r = \tan\theta$, which is substituted to Formula (4) above, then $\Delta x$ can be represented by Formula (5) below.

$$\Delta x = r\Delta\theta \times \frac{\tan\theta}{\theta} \times \frac{\sqrt{1+\tan^2\theta}}{\cos\theta} = r\Delta\theta \times \frac{\tan\theta}{\theta\cos^2\theta} \tag{5}$$

Thus, the ratio between the pitch at (r, x) and the pitch $r\Delta\theta$ at intersection point Q can be represented by Formula (6) below.

$$\frac{\Delta x}{r\Delta\theta} = \frac{\tan\theta}{\theta\cos^2\theta} \tag{6}$$

Relationship between $\theta$ and $\Delta x/r\Delta\theta$ obtained based on Formula (6) above is summarized in Table 1 below.

TABLE 1

| | $\theta$ | | | | |
|---|---|---|---|---|---|
| | 1.0° | 2.0° | 5.0° | 10.0° | 15.0° |
| $\Delta x/r\Delta\theta$ | 1.0004 | 1.002 | 1.01 | 1.04 | 1.10 |

Here, assuming pitch $P_1$ of the diffraction members of first diffraction grating 20 to be 0.8 µm, the width of each diffraction member to be 3 µm, and one pixel width of radiation image detector 3 to be 120 µm, if the phase of first diffraction grating 20 is shifted about 1/12 of the pitch, it is thought to be undesirable that a signal of different phase component is mixed in the same pixel. Given that the radiation beam spreads from the central axis to X direction (direction orthogonal to the diffraction members), it is preferable that the positional displacement is limited to 8/12×1/2=8/24=0.333 µm or less.

That is, if the pitch of the diffraction members on central axis C is assumed to be 8 µm, the distance between the centers of diffraction members at each end in one pixel in a peripheral portion of the radiation beam is $\Delta x/r\Delta\theta \times 8 \times 4$.

Accordingly, if $\Delta x/r\Delta\theta \times 8 \times 4 - 32 < 0.333$, the condition described above is met.

Thus, $\Delta x/r\Delta\theta < 1.010$.

Accordingly, it is known from Table 1 above that one-side spread angle $\theta$ of the radiation beam in X direction needs to be limited to 5° or less.

For example, if r=1000 mm, 2×1000×tan 5°=175 mm, thus the width of radiation beam emitted from one radiation source 1a in X direction on first diffraction grating 20 needs to be limited to 175 mm or less.

So far, the description has been made of a case in which one pixel width of radiation image detector 3 is assumed to be about 120 µm. Now, the discussion will be made of a case in which one pixel width of radiation image detector 3 is assumed to be about 80 µm. Here, the pitch and width of the diffraction members are assumed to be identical to those described above.

In this case, when the phase of first diffraction grating 20 is shifted about 1/8 of the pitch, it is thought to be undesirable that a signal of different phase component is mixed in the same pixel. Given that the radiation beam spreads from the central axis to X direction (direction orthogonal to the diffraction members), it is preferable that the positional displacement of diffraction members in one pixel is limited to 8/8×1/2=8/16=0.5 μm or less.

That is, if the pitch of the diffraction members on central axis C is assumed to be 8 μm, the distance between the centers of diffraction members at each end in one pixel in a peripheral portion of the radiation beam is Δx/rΔθ×8×4.

Accordingly, if Δx/rΔθ×8×4−32<0.5, the condition described above is met.

Thus, Δx/rΔθ<1.016.

Accordingly, it is known from Table 1 above that one-side spread angle θ of the radiation beam in X direction needs to be limited to 6° or less.

For example, if r=1000 mm, 2×1000×tan 6°=210 mm, thus the width of the radiation beam emitted from one radiation source 1a in X direction on first diffraction grating 20 needs to be limited to 210 mm or less.

The above discussion shows that the pitch of the diffraction members does not depend on the restrictions of spread angle θ of the radiation beam.

In the discussion above, the description has been made of a case in which subject 10 is placed between radiation emission unit 1 and first diffraction grating 20. Also, in a case in which subject 10 is placed between first diffraction grating 20 and second diffraction grating 30, the self-image of first diffraction grating 20 produced at the position of second diffraction grating 30 is deformed by subject 10. Therefore, also in this case, an image signal of a phase component modulated due to subject 10 can be detected by radiation image detector 3. That is, in the tomosynthesis radiographing apparatus according to the present embodiment, subject 10 may be placed between radiation emission unit 1 and first diffraction grating 20 or between first diffraction grating 20 and second diffraction grating 30.

Also in the second embodiment, radiation emission unit 1 may be structured in various ways as described in the first embodiment. When using a radiation emission unit having multi-slit 16d shown in FIG. 10, however, it is necessary to dispose the multi-slit so as to become parallel to diffraction members 22, 32 of first diffraction grating 20 and second diffraction grating 30. Further, it is preferable that radiation emission unit 1 is a unit that limits each radiation exposure range such that each exposure range of radiation passed through the collimator overlap with each other without any space between them at a position of subject 10 and at an angle that substantially does not influence a diffraction property of first diffraction grating 20 in a peripheral portion of an exposure range at a position of first diffraction grating 20.

In radiation emission unit 16 shown in FIG. 10, when metal target 16c is formed with metal wires, the wires need to be arranged so as to become parallel to diffraction members 22, 32 of first diffraction grating 20 and second diffraction grating 30.

Further, in radiation emission unit 16 shown in FIG. 10, when cold cathode electron source 16a is formed with linear cold cathode electron sources, the linear cold cathode electron sources need to be arranged so as to become parallel to diffraction members 22, 32 of first diffraction grating 20 and second diffraction grating 30.

When the structure shown in FIG. 10 or any other modifications thereof described above is used, a Talbot-Lau interferometer is formed.

Figure 14:
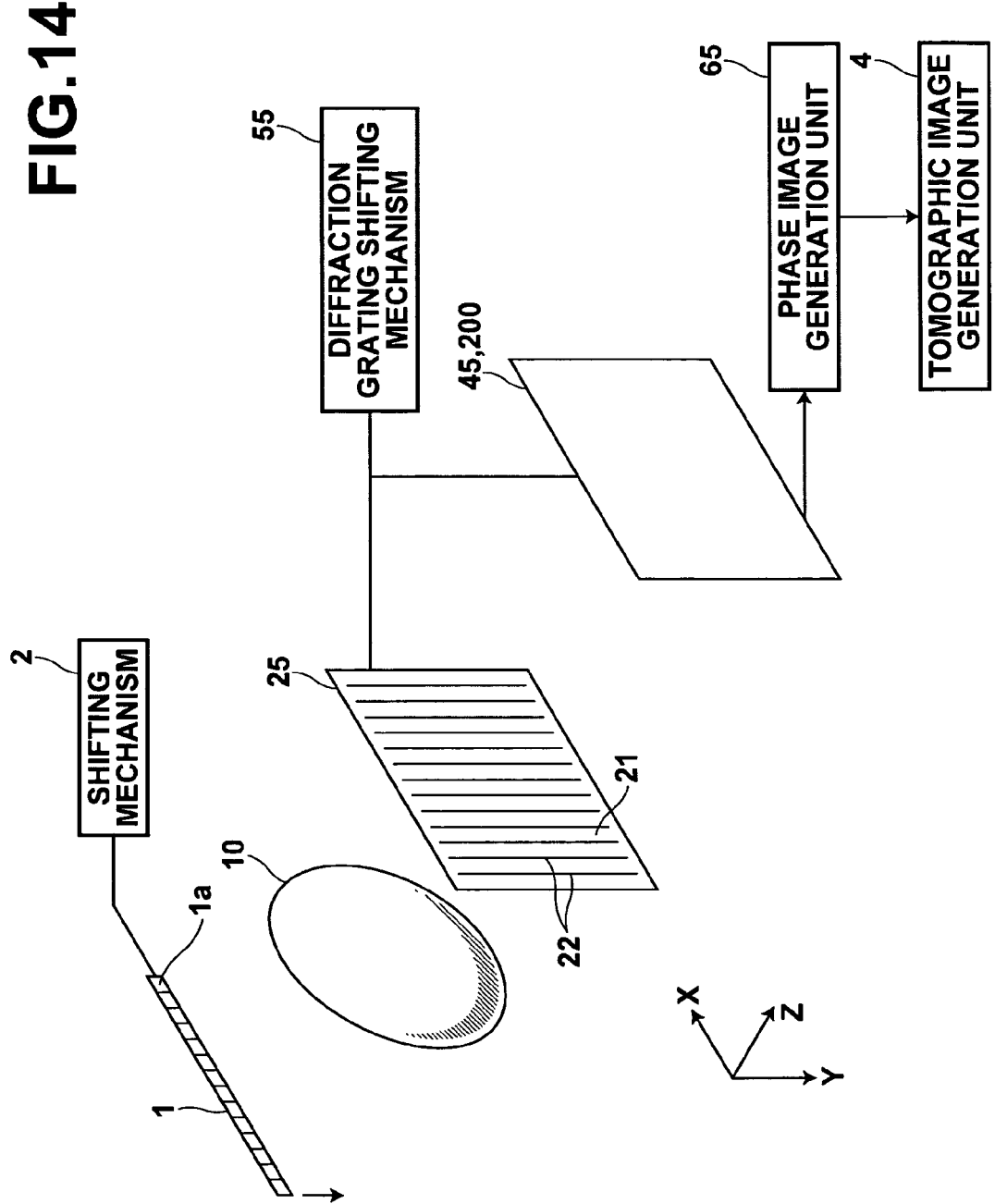
FIG. 14 is a schematic construction diagram of a third embodiment of the tomosynthesis radiographing apparatus of the present invention.
Figure 15:
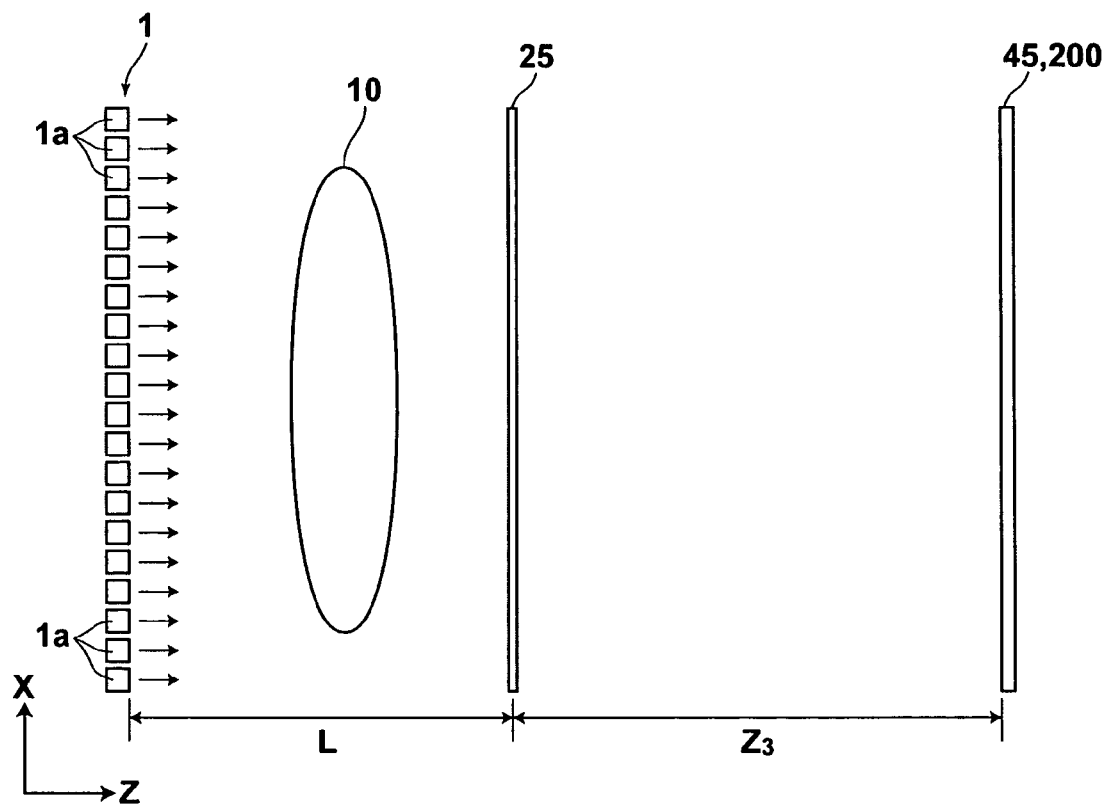
FIG. 15 is a top view of the tomosynthesis radiographing apparatus shown in FIG. 14.

Next, a third embodiment of the tomosynthesis radiographing apparatus of the present invention will be described. FIG. 14 schematically illustrates the structure of the tomosynthesis radiographing apparatus according to the third embodiment. FIG. 15 is a top view (X-Z sectional view) of the tomosynthesis radiographing apparatus shown in FIG. 14. The thickness direction in FIG. 15 corresponds to Y direction in FIG. 14.

The tomosynthesis radiographing apparatus according to the third embodiment uses periodic information imaging radiation image detector 45 instead of radiation image detector 3 and second diffraction grating 30 of tomosynthesis radiographing apparatus according to the second embodiment.

As illustrated in FIG. 14, the tomosynthesis radiographing apparatus according to the third embodiment includes radiation emission unit 1 that emits radiation onto subject 10, diffraction grating 25 configured to be exposed to the radiation transmitted through subject 10 and to produce Talbot interference or Talbot-Lau interference by the exposure, periodic information imaging radiation image detector 45 that detects periodic information of the radiation diffracted by diffraction grating 25, diffraction grating shifting mechanism 55 that shifts diffraction grating 25 and periodic information imaging radiation image detector 45 in a direction orthogonal to linear electrodes of detector 45 (X direction in FIG. 14) along respective planes, phase image generation unit 65 that generates a phase image based on an image signal detected by periodic information imaging radiation image detector 45, and tomographic image generation unit 4 that generates a tomographic image based on the phase image generated by the phase image generation unit 65.

Radiation emission unit 1 has an identical structure to those of the first embodiment and second embodiment.

Diffraction grating 25 has an identical structure to that of the first diffraction grating in the tomosynthesis radiographing apparatus according to the second embodiment.

In the tomosynthesis radiographing apparatus according to the third embodiment, a Talbot interferometer is constructed with diffraction grating 25 and periodic information imaging radiation image detector 45. Conditions for the Talbot interferometer will be described. First, coherence length l is calculated in the following manner.

$$l = \frac{\lambda}{a/(L+Z_3)} \quad (7)$$

where,
λ: wavelength of radiation (generally, center wavelength)
a: aperture diameter of radiation source in a direction substantially orthogonal to diffraction members.
L: distance from radiation source (if a slit is used in the radiation emission unit, from the position of the slit) to diffraction grating 25 (FIG. 15)
$Z_3$: distance from diffraction grating 25 to periodic information imaging radiation image detector 45 (FIG. 15)

Distance $Z_3$ between diffraction grating 25 and periodic information imaging radiation image detector 45 needs to substantially satisfy the following condition, on the assumption that diffraction grating 25 is a phase diffraction grating.

$$Z_3 = \left(m + \frac{1}{2}\right)\frac{P_1^2}{\lambda} \quad (8)$$

where, m is 0 or a positive integer, and λ is the wavelength of radiation.

If diffraction grating 25 is an amplitude diffraction grating, the following condition needs to be satisfied.

$$Z_3 = (m+1)\frac{P_1^2}{\lambda} \quad (9)$$

where, m is 0 or a positive integer, and λ is the wavelength of radiation.

Figure 16:
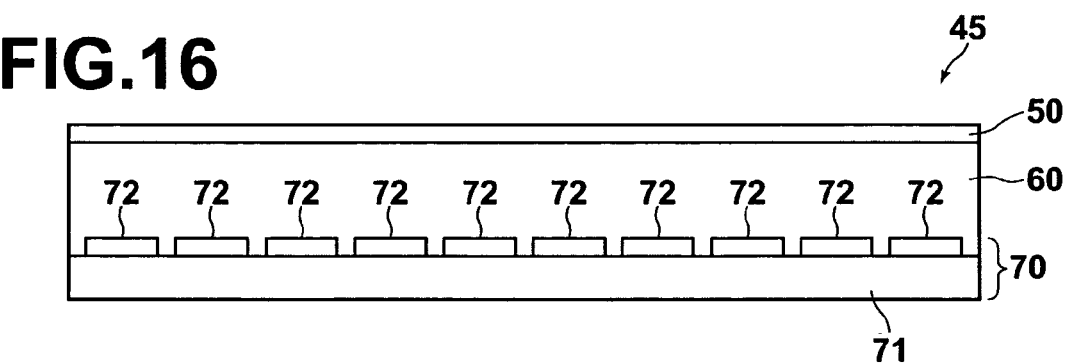
FIG. 16 is a sectional view of a periodic information imaging radiation image detector in the tomosynthesis radiographing apparatus according to the third embodiment.

The structure of periodic information imaging radiation image detector 45 in the tomosynthesis radiographing apparatus of the present embodiment will now be described in detail. FIG. 16 is a partial sectional view of periodic information imaging radiation image detector 45.

As illustrated in FIG. 16, periodic information imaging radiation image detector 45 includes active matrix substrate 70, semiconductor layer 60 formed on substantially the entire surface of the active matrix substrate 70, and upper electrode 50.

Semiconductor layer 60 has electromagnetic wave conductivity and generates charges therein when exposed to radiation. As for semiconductor layer 60, for example, a selenium based amorphous Se film with a thickness of 10 to 1500 μm may be used. Alternatively, $PbI_2$, $HgI_2$, Cd (Zn)Te, $Bi_{12}TiO_{20}$, $Bi_{12}SiO_{20}$, or $Bi_{12}GeO_{20}$ may also be used. Semiconductor layer 60 is formed on active matrix substrate 70 by a vacuum deposition method or the like.

Upper electrode 50 is formed of a conductive material having a low resistance, such as Au, Al, or the like, with a thickness capable of transmitting irradiated radiation. Note that intermediate layers may be provided between upper electrode 50 and semiconductor layer 60. Such intermediate layers include a charge transport layer for preventing charge injection from upper electrode 50 and allowing charges of those generated in the semiconductor layer having opposite polarity to that of injected charges to reach upper electrode 50, a crystallization prevention layer for preventing crystallization of the amorphous Se, and the like.

As illustrated in FIG. 16, active matrix substrate 70 includes glass substrate 71 on which multiple unit elements 72, which include charge collection electrodes and switch elements corresponding to pixels forming radiation image of a subject, are disposed two-dimensionally.

Figure 17:
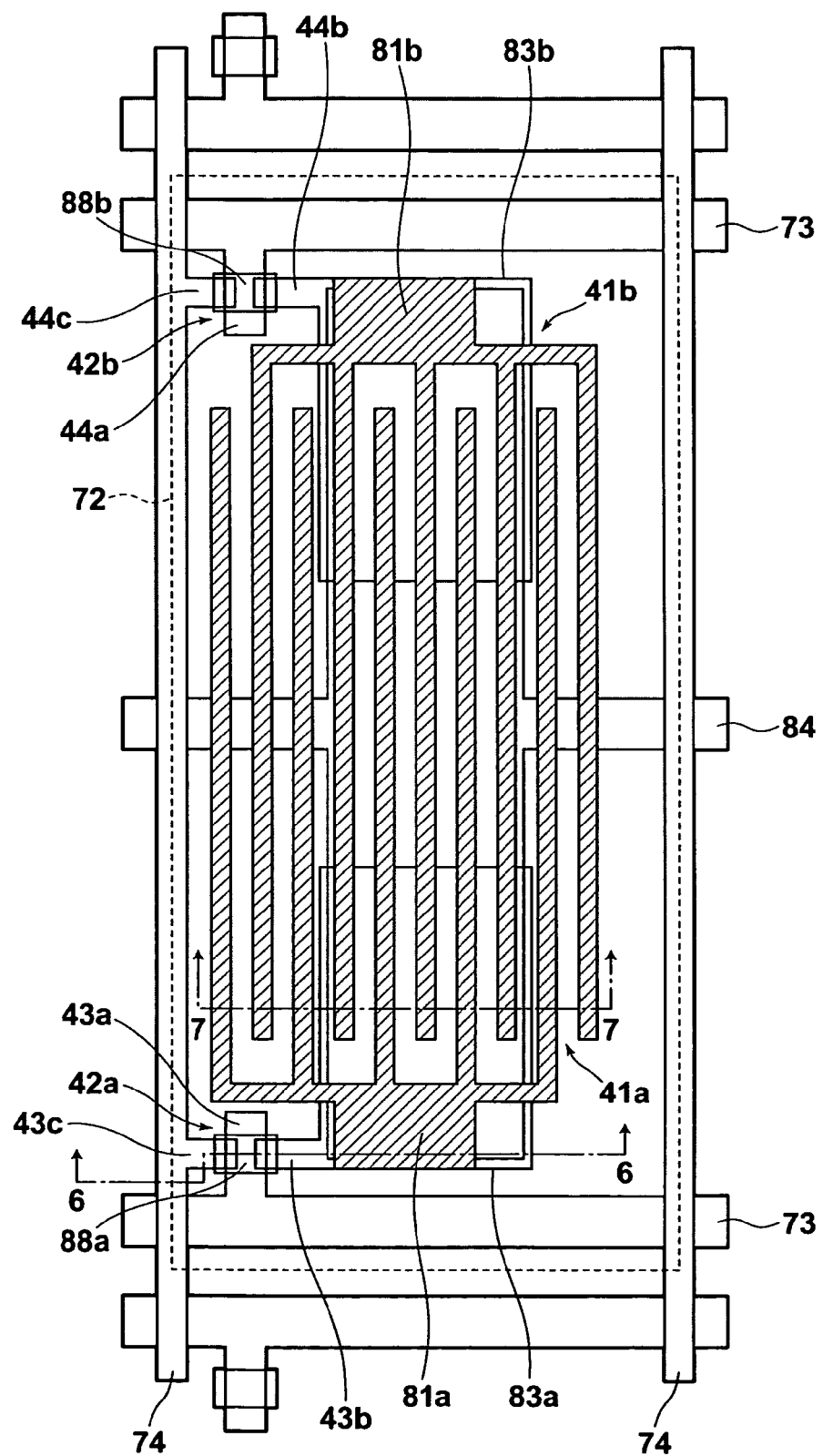
FIG. 17 is a partial plan view of the periodic information imaging radiation image detector.
Figure 18:
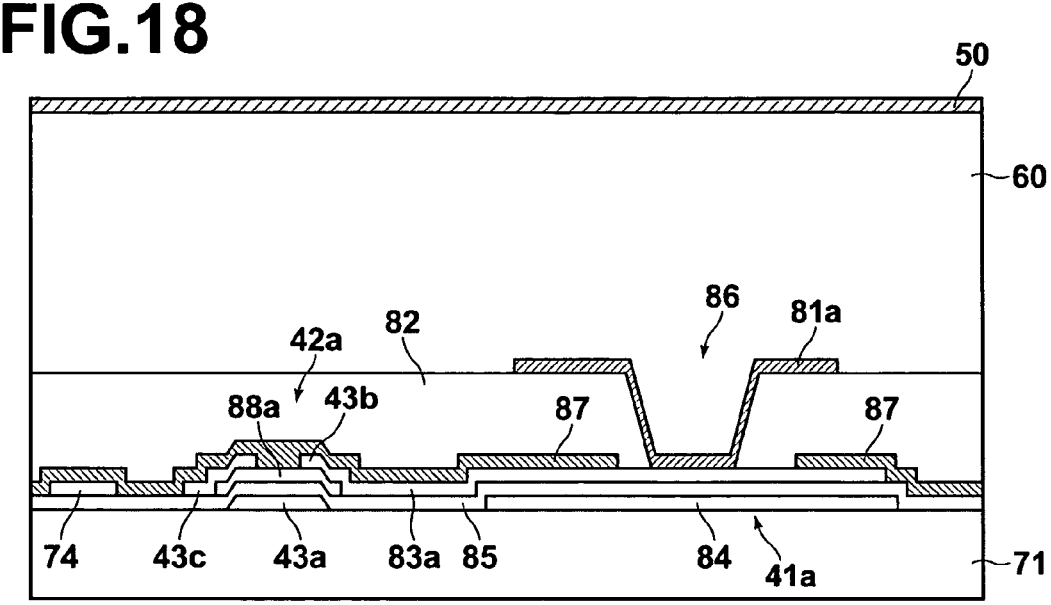
FIG. 18 is a sectional view of the periodic information imaging radiation image detector taken along the line 6-6 in FIG. 17.
Figure 19:
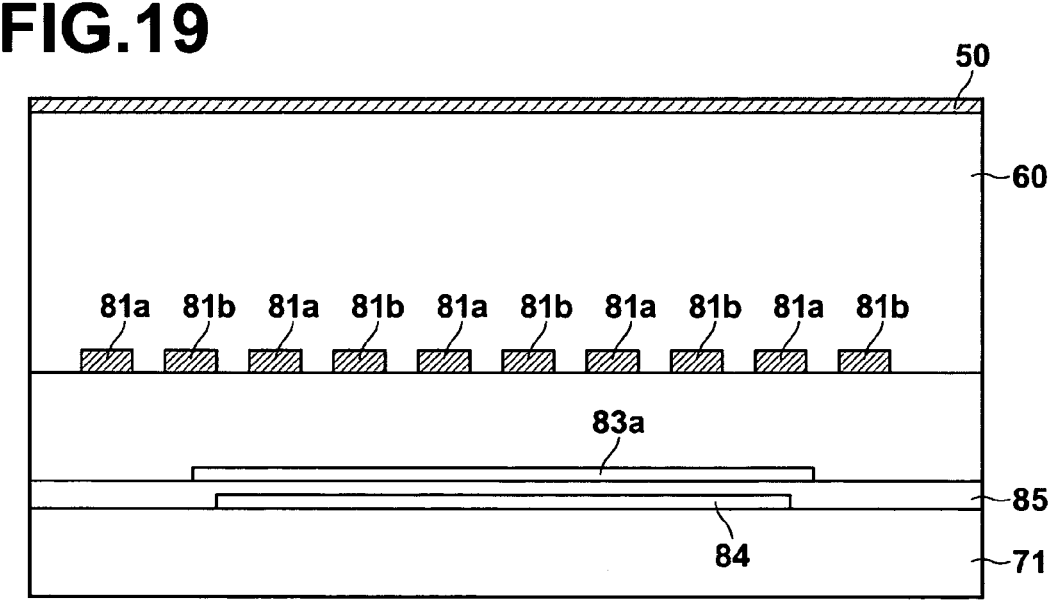
FIG. 19 is a sectional view of the periodic information imaging radiation image detector taken along the line 7-7 in FIG. 17.

The structure of each pixel or sub-pixel of periodic information imaging radiation image detector 45 will now be described in detail. The term "sub-pixel" as used herein refers to a pair of two linear electrode groups alternately disposed such that the phase of the arrangement periodic become opposite to each other. FIG. 17 is a plan view of periodic information imaging radiation image detector 45, FIG. 18 is a sectional view of periodic information imaging radiation image detector 45 taken along the line 6-6 in FIG. 17, and FIG. 19 is a sectional view of periodic information imaging radiation image detector 45 taken along the line 7-7 in FIG. 17.

Periodic information imaging radiation image detector 45 includes a charge collection electrode, constituted by first linear electrode group 81a and second linear electrode group 81b, for collecting charges generated in semiconductor layer 60, first storage capacitor 41a for storing charges collected by first linear electrode group 81a, second storage capacitor 41b for storing charges collected by second linear electrode group 81b, a first TFT switch 42a for reading out the charges stored in first storage capacitor 41a, a second TFT switch 42b for reading out the charges stored in second storage capacitor 41b.

Figure 20:
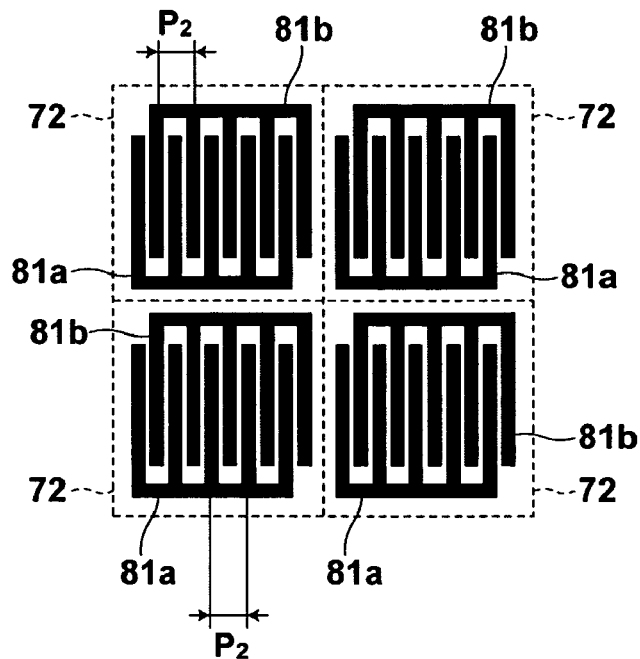
FIG. 20 is a schematic view of first linear electrode groups and second linear electrode groups of unit elements corresponding to four pixels.

FIG. 20 schematically illustrates first linear electrode groups 81a and second linear electrode groups 81b of unit elements 72 corresponding to four pixels. Each of first linear electrode group 81a and second linear electrode group 81b includes multiple linear electrodes periodically disposed with a pitch of $P_2$. A linear electrode of second linear electrode group 81b is disposed between linear electrodes of first linear electrode group 81a such that the phase of the arrangement periodic of linear electrodes of first linear electrode groups 81a and the phase of the arrangement periodic of linear electrodes of second linear electrode group 81b are shifted by π (180°=a half of the pitch) from each other. As illustrated in FIG. 20, linear electrodes of first linear electrode group 81a are connected to each other, and linear electrodes of second linear electrode group 81b are connected to each other. Preferably, the connection wire connecting the linear electrodes is provided on a different plane from that of the linear electrodes so as not to function as an electrode, but the influence of the connection wire may be substantially reduced to a negligible level by reducing the width of the connection wire.

Arrangement pitch $P_2$ of linear electrodes of first linear electrode group 81a and arrangement pitch $P_2$ of linear electrodes of second linear electrode group 81b are set to a value in the range from 2 to 15 μm. The width of each linear electrode of first linear electrode group 81a and the width of each linear electrode of second linear electrode group 81b are set to a value in the range from 1 to 14 μm.

The ratio between distance L from radiation source 1a to diffraction grating 25 and pitch $P_1$ in diffraction grating 25 may be set substantially equal to the ratio between distance from radiation source 1a to periodic information imaging radiation image detector 40, $L+Z_3$, and pitch $P_2$ of linear electrodes of periodic information imaging radiation image detector 45.

For example, first linear electrode group 81a and second linear electrode group 81b may be formed of an amorphous transparent conductive oxide film.

Note that intermediate layers may be provided between first linear electrode group 81a and second linear electrode group 81b and semiconductor layer 60. Such intermediate layers include a charge transport layer for preventing charge injection from the electrodes and allowing charges generated in semiconductor layer 60 to be collected by first linear electrode group 81a and second linear electrode group 81b, a crystallization prevention layer for preventing crystallization of the amorphous Se, and the like.

First storage capacitor 41a is constituted by connection electrode 83a, gate insulation film 85, and charge storage capacitor electrode 84, in which gate insulation film 85 acts as a dielectric body and charges are stored between connection electrode 83a and charge storage capacitor electrode 84. Second storage capacitor 41b is constituted by connection electrode 83b, gate insulation film 85, and charge storage capacitor electrode 84, in which gate insulation film 85 acts as a dielectric body and charges are stored between connection electrode 83b and charge storage capacitor electrode 84.

First TFT switch 42a is constituted by gate electrode 43a formed by extending scanning wire 73, to be described later, drain electrode 43b formed by extending connection electrode 83a, source electrode 43c formed by extending data wire 74, to be described later, gate insulation film 85, semiconductor film 88a, and the like. Second TFT switch 42b is constituted by gate electrode 44a formed by extending scanning wire 73, drain electrode 44b formed by extending connection electrode 83b, source electrode 44c formed by extending data wire 74, gate insulation film 85, semiconductor film 88b, and the like. For example, gate insulation film 85 is formed of $SiN_x$, $SiO_x$, or the like. Semiconductor films 88a, 88b are channel sections of first and second TFT switches 42a, 42b, which are current paths connecting data wire 74 to connection electrodes 83a, 83b.

Insulation protection film 87 is formed so as to cover first storage capacitor 41a and second storage capacitor 41b, first TFT switch 42a and second TFT switch 42b, data wire 74, and the like. Contact holes 86 are formed in insulation protection film 87 at a connection section between first linear electrode group 81a and connection electrode 83a, and at a connection section between second linear electrode group 81b and connection electrode 83b.

Interlayer insulation film 82 is formed on insulation protection film 87 and contact holes 86 are formed through interlayer insulation film 82, through which first linear electrode group 81a is connected to connection electrode 83a, and second linear electrode group 81b is connected to connection electrode 83b. Interlayer insulation film 82 is an organic insulation film to electrically insulate and isolate first TFT switch 42a from second TFT switch 42b. For example, an acrylic resin may be used as the material of the organic insulation film.

As illustrated in FIG. 17, scanning wires 73 and data wires 74 are electrode wires disposed in a grid pattern, and first TFT switch 42a or second TFT switch 42b is formed adjacent to each intersection point. Different scanning wires 73 are connected to first TFT switch 42a and second TFT switch 42b, and first TFT switch 42a and second TFT switch 42b are configured to be ON/OFF controlled independently.

A readout circuit (not shown) constituted by an amplifier for detecting a signal charge flowing out to data wire 74 is connected at the end of data wire 74. A gate driver (not shown) that outputs control signals for independently controlling first TFT switch 42a and second TFT switch 42b is connected to scanning wire 73.

As described above, diffraction grating shifting mechanism 55 is a mechanism for shifting diffraction grating 25 and periodic information imaging radiation image detector 45 in X direction. For example, diffraction grating 25 and periodic information imaging radiation image detector 45 may be shifted by 1/n (n is an integer not less than two) of arrangement pitch $P_2$ of the linear electrodes of periodic information imaging radiation image detector 45 to take a radiation image at each position, whereby image signals of n-types of phase components may be obtained. It is preferable, for example, to shift periodic information imaging radiation image detector 45 such that image signals corresponding to four or six types of phase components are obtained. When the charge collection electrode is formed of first linear electrode group 81a and second linear electrode group 81b, as in the present embodiment, four types of phase components may be obtained by shifting detector 40 by ½ of arrangement pitch $P_2$ and six types of phase components may be obtained by shifting detector 45 by ⅓ of arrangement pitch $P_2$. When forming a phase image with signals corresponding to two types of phase components, diffraction grating shifting mechanism 55 is not required.

Next, an operation of the tomosynthesis radiographing apparatus of the present embodiment for recording a radiation image to and reading out from the periodic information imaging radiation image detector will be described.

First, subject 10 is placed between radiation emission unit 1 and diffraction grating 25 (FIG. 14). In the tomosynthesis radiographing apparatus according to the present embodiment, subject 10 is placed between radiation emission unit 1 and diffraction grating 25, but subject 10 may be placed between diffraction grating 25 and periodic information imaging radiation image detector 45. In this case, the distance from the subject to periodic information imaging radiation image detector 45 becomes shorter and the magnification rate is reduced, which allows the apparatus to be easily installed in an existing radiography room.

Next, radiation is emitted from each radiation source 1a of radiation emission unit 1 simultaneously onto diffraction grating 25. The radiation irradiated to diffraction grating 25 passes through diffraction grating 25. At this time, a Talbot effect is produced in diffraction grating 25. The Talbot effect as used herein refers to that, when a plane wave passes through a phase diffraction grating, a self-image of the diffraction grating is formed at the distance given by $Z_3$ described above. In the case described above, the radiation is phase shifted by subject 10, so that the wave front of the radiation incident on diffraction grating 25 is distorted. Accordingly, the self-image of diffraction grating 25 is deformed according to the distortion.

Then, with a positive voltage being applied to upper electrode 50 of periodic information imaging radiation image detector 45 by a voltage source, the radiation representing a self-image formed by the Talbot effect of diffraction grating 25 in the manner as described above is irradiated to periodic information imaging radiation image detector 45 from the side of upper electrode 50. In the tomosynthesis radiographing apparatus of the present embodiment, periodic information imaging radiation image detector 45 is disposed such that upper electrode 50 is oriented to the side of radiation emission unit 1 and the length direction of each linear electrode of first and second linear electrode groups 81a and 81b corresponds to the length direction of each diffraction member 22 of diffraction grating 25.

The radiation irradiated to periodic information imaging radiation image detector 45 transmits through upper electrode 50 and exposes semiconductor layer 60. Then, semiconductor layer 60 generates charge pairs by the exposure of the radiation, and negative charges of the charge pairs are combined with positive charges charged on upper electrode 50 and dissolved, while positive charges of the charge pairs are collected by first and second linear electrode groups 81a, 81b of each unit element 72, and stored in first and second storage capacitors 41a, 41b.

Figure 21:
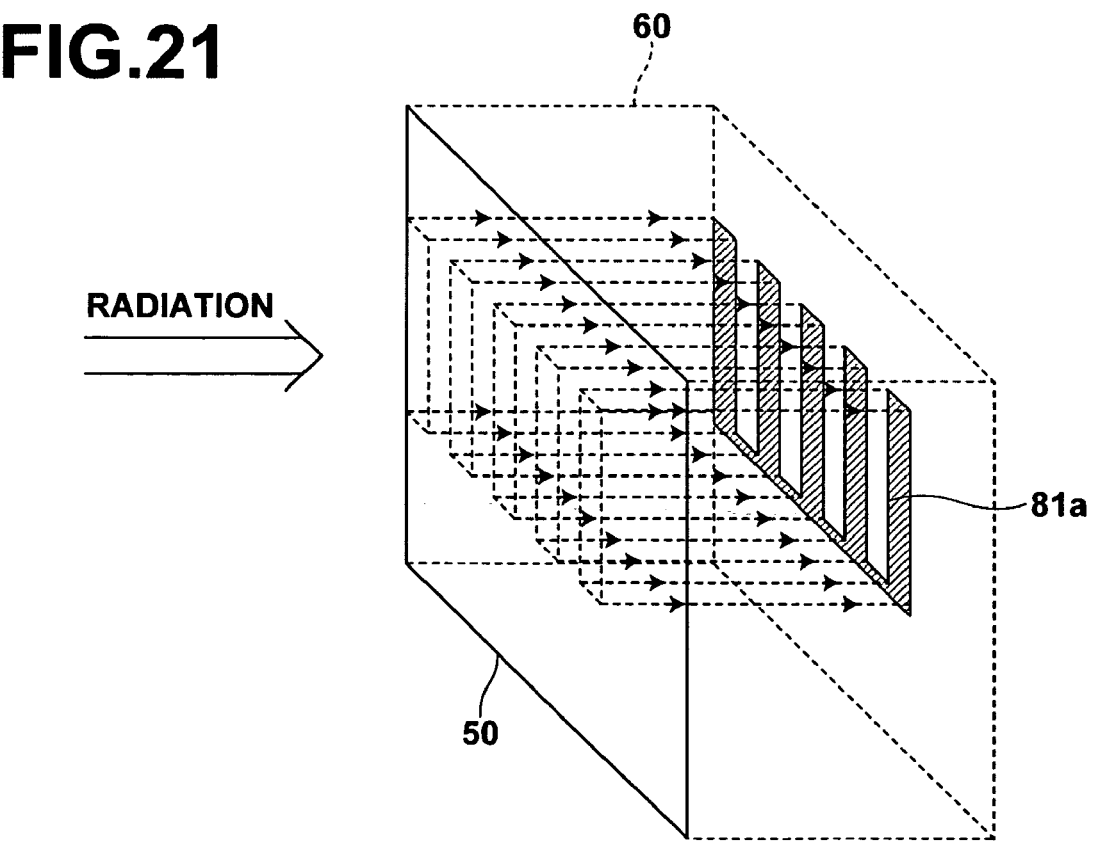
FIG. 21 illustrates an electric field formed in a semiconductor layer by the first linear electrode group.

Now, in periodic information imaging radiation image detector 45 of the tomosynthesis radiographing apparatus of the present embodiment, the charge collection electrode for collecting charges generated in semiconductor layer 60 is constituted by first linear electrode group 81a and second linear electrode group 81b. Therefore, when a voltage is applied to upper electrode 50 in the manner as described above, electric fields are formed in semiconductor layer 60 toward first and second linear electrode groups substantially parallel to each other, i.e., substantially perpendicular to the surface of upper electrode 50, as illustrated by dotted arrows in FIG. 21. The charges generated in semiconductor layer 60 are collected by each linear electrode along the electric field without diffusing, so that first and second linear electrode groups 81a, 81b perform a function equivalent to that of the combination of an amplitude diffraction grating and a detector provided in the latter stage of the grating. Accordingly, charges representing image contrast generated by the superimposition of a self-image of the deformed diffraction grating 25 and a virtual diffraction grating formed by first linear electrode group 81a are stored in first charge capacitor 41a, and charges representing image contrast generated by the superimposition of a self-image of the deformed diffraction grating 25 and a virtual diffraction grating formed by second linear electrode group 81b are stored in second charge capacitor 41b. The image contrast described above generally takes the form of Moire fringes. As described above, first linear electrode group 81a and second linear electrode group 81b are phase shifted by π from each other, thus signals corresponding to two types of phase components phase shifted from each other by π are detected by periodic information imaging radiation image detector 45.

Then, control signals for turning ON first TFT switches 42a are sequentially outputted from the not shown gate driver to each scanning wire 73 connected to first TFT switches 42a. Then, first TFT switches 42a are turned ON according to the control signals outputted from the gate driver, and charges stored in first storage capacitor 41a of each unit element 72 are read out to data wire 74. The charge signal flowing out to data wire 74 is detected by the charge amplifier of a not shown readout circuit as an image signal corresponding to a first phase component.

Then, control signals for turning ON second TFT switches 42b are sequentially outputted from the not shown gate driver to each scanning wire 73 connected to second TFT switches 42b. Then, second TFT switches 42b are turned ON according to the control signals outputted from the gate driver, and charges stored in second storage capacitor 41b of each unit element 72 are read out to data wire 74. The charge signal flowing out to data wire 74 is detected by the charge amplifier of a not shown readout circuit as an image signal corresponding to a second phase component.

Thereafter, in association with the shift of diffraction grating 25 and periodic information imaging radiation image detector 45 by diffraction grating shifting mechanism 55, image recording in the detector 45 and image signal reading from the detector 45 are performed with respect to each predetermined position, whereby image signals corresponding to the first and second phase components are detected with respect to each predetermined position.

Image signals detected in the manner as described above are inputted to phase image generation unit 65. Then, phase image generation unit 65 generates a partial phase image with respect to each detection range of periodic information imaging radiation image detector 45 based on image signals of a plurality of phase components detected by periodic information imaging radiation image detector 45 in each detection range corresponding to the exposure range of radiation emitted from each radiation source 1a. That is, a partial phase image corresponding to each radiation source 1a is generated. Thereafter, the partial phase images are combined to produce a complete phase image.

Then, radiation emission unit 1 is shifted in Y direction, as in the first embodiment; and at each predetermined position, radiation is emitted from each radiation source 1a of radiation emission unit 1 and diffraction grating 25 and periodic information imaging radiation image detector 45 are shifted, whereby a phase image at each position of radiation emission unit 1 is sequentially generated.

Image signals representing a plurality of phase images generated in phase image generation unit 65 are inputted to tomographic image generation unit 4. Tomographic image generation unit 4 performs shift processing on the inputted plurality of image signals according to a desired cross-sectional position of the subject and generates a tomographic image according to the cross-sectional position by adding the shift processed image signals, as in the first embodiment.

Next, a modification of periodic information radiographing image detector 45 of the tomosynthesis radiographing apparatus of the third embodiment will be described.

Figure 22:
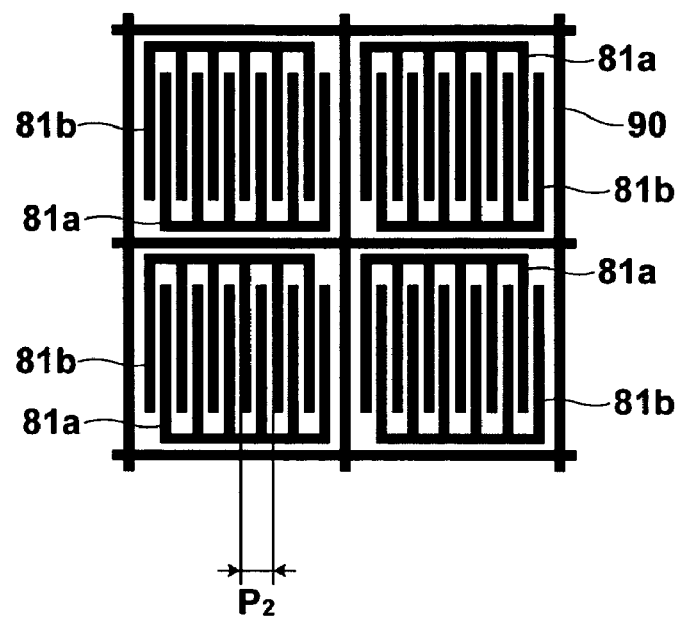
FIG. 22 illustrates a modification of the periodic information imaging radiation image detector in the tomosynthesis radiographing apparatus according to the third embodiment.

In addition to first linear electrode group 81a and second linear electrode group 81b of periodic information imaging radiation image detector 45 shown in FIG. 20, constant potential linear electrode 90 may be provided in a grid pattern enclosing the charge collection electrode, constituted by first and second linear electrode groups 81a, 81b, of each unit element 72, as illustrated in FIG. 22. If a gap is present between charge collection electrodes, electric fields are bent and a charge is collected from a portion where the linear electrode is not present, whereby phase component contamination occurs. Consequently, the provision of constant potential linear electrode 90 to which a constant potential is applied allows stabilization of the electric fields and prevention of the contamination described above. A potential that does not cause a large potential difference with an adjacent charge collection electrode is applied to constant potential linear electrode 90. That is, substantially the same potential as that of the charge collection electrode is applied. More specifically, constant potential linear electrode 90 is set to a ground potential or a value close to the ground potential. Where constant potential linear electrode 90 is provided, it is preferable to arrange and dispose first linear electrode group 81a and second linear electrode group 81b in the manner shown in FIG. 22.

In periodic information imaging radiation image detector 45 of the present embodiment, first linear electrode group 81a and second linear electrode group 81b, phase shifted by n from each other, are provided in each unit element 72 as the charge collection electrode. The shape of the charge collection electrode is not limited to this.

Figure 23:
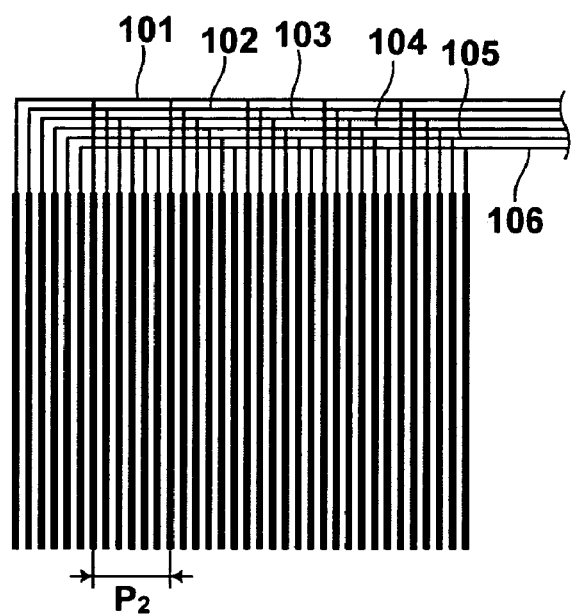
FIG. 23 illustrates a modification of the periodic information imaging radiation image detector in the tomosynthesis radiographing apparatus according to the third embodiment.

For example, first to sixth linear electrode groups 101 to 106, each having multiple linear electrodes arranged with pitch $P_2$, may be disposed such that the phase of the arrangement periodic of linear electrodes of each linear electrode group is shifted by π/3 from each other, as illustrated in FIG. 23. More specifically, first to sixth linear electrode groups 101 to 106 may be disposed such that, when the phase of first linear electrode group 101 is 0, the phase of second linear electrode group 102 is π/3, the phase of third linear electrode group 103 is 2π/3, the phase of fourth linear electrode group 104 is π, the phase of fifth linear electrode group 105 is 4π/3, and the phase of sixth linear electrode group 106 is 5π/3.

Formation of the charge collection electrode in the manner illustrated in FIG. 23 to read out charges collected by first to sixth linear electrode groups 101 to 106 with respect to each linear electrode group allows acquisition of image signals corresponding to six types of phase components having different phases by one radiographing operation. Accordingly, diffraction grating shifting mechanism 55 is not required.

Figure 24:
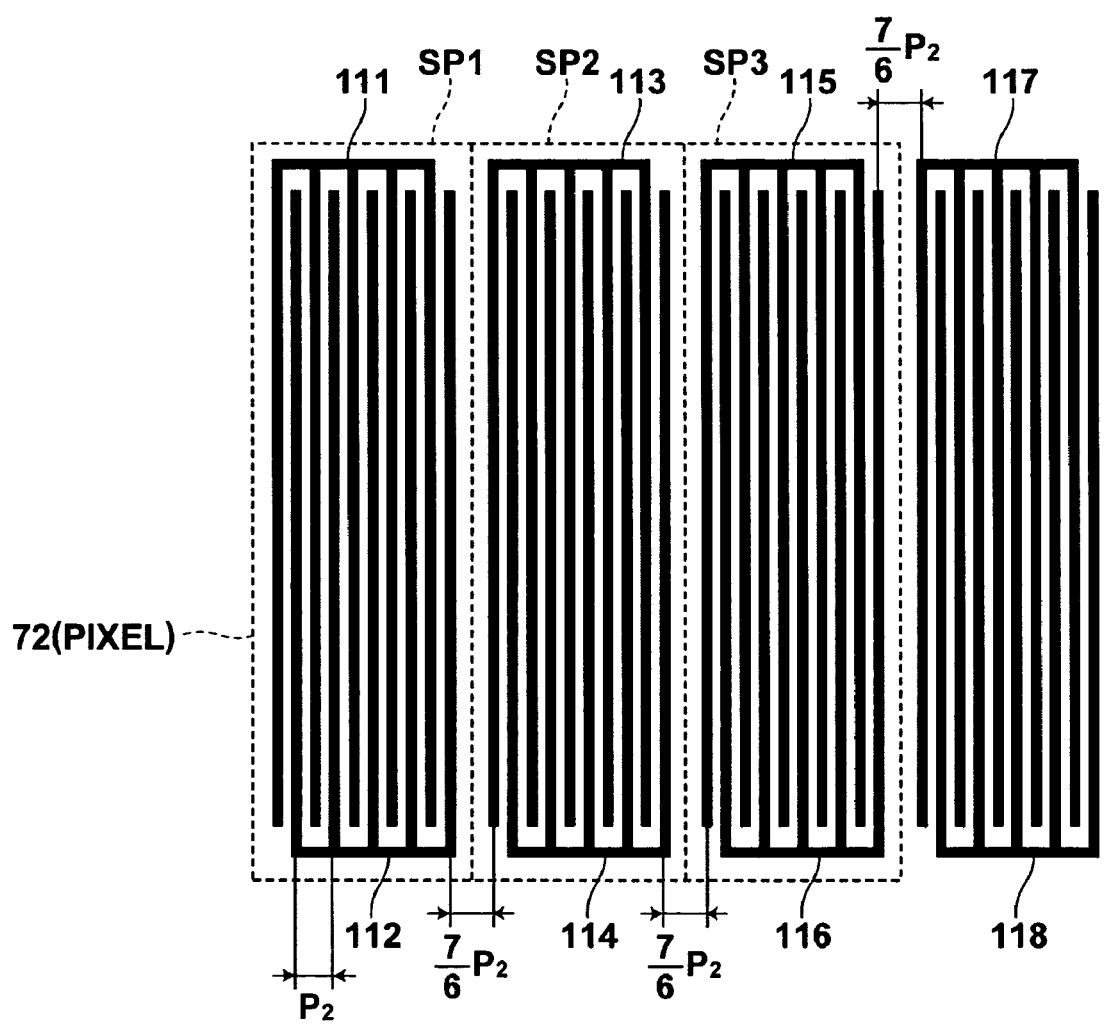
FIG. 24 illustrates a modification of the periodic information imaging radiation image detector in the tomosynthesis radiographing apparatus according to the third embodiment.

Further, as illustrated in FIG. 24, a pixel corresponding to one unit element 72 may be divided into a plurality of sub-pixels (here, three sub-pixels) and linear electrode groups having different phases may be disposed in each sub-pixel. In the present embodiment, the sub-pixel refers to a pair of two linear electrode groups alternately disposed such that the phase of the arrangement periodic becomes opposite to each other.

More specifically, in the modification shown in FIG. 24, first linear electrode group 111 in which linear electrodes are arranged with pitch $P_2$ and second linear electrode group 112 in which linear electrodes are arranged with pitch $P_2$ are disposed in sub-pixel SP1 so as to have a phase difference of π from each other, third linear electrode group 113 in which linear electrodes are arranged with pitch $P_2$ and fourth linear electrode group 114 in which linear electrodes are arranged with pitch $P_2$ are disposed in sub-pixel SP2 so as to have a phase difference of $\pi$ from each other, and fifth linear electrode group 115 in which linear electrodes are arranged with pitch $P_2$ and sixth linear electrode group 116 in which linear electrodes are arranged with pitch $P_2$ are disposed in sub-pixel SP3 so as to have a phase difference of $\pi$ from each other. Then, adjacent linear electrode groups of sub-pixel SP1 and sub-pixel SP2 are disposed at a distance of (7/6)×pitch $P_2$, and adjacent linear electrode groups of sub-pixel SP2 and sub-pixel SP3 are disposed at a distance of (7/6)×pitch $P_2$, whereby the phase is shifted by $4\pi/3$ between sub-pixels. Arrangement of the linear electrode groups in one pixel in the manner shown in FIG. 24 results in that, when the phase of first linear electrode group 111 is 0, the phase of second linear electrode group 112 is $\pi$, the phase of third linear electrode group 113 is $4\pi/3$, the phase of fourth linear electrode group 114 is $\pi/3$, the phase of fifth linear electrode group 115 is $2\pi/3$, and the phase of sixth linear electrode group 116 is $5\pi/3$. Note that linear electrode group 117 and linear electrode group 118 are the linear electrode groups of adjacent pixel.

Formation of the charge collection electrode in the manner illustrated in FIG. 24 to read out charges collected by first to sixth linear electrode groups 111 to 116 with respect to each linear electrode group allows acquisition of image signals corresponding to six types of phase components by one radiographing operation. The structure of charge collection electrode shown in FIG. 23 also allows acquisition of image signals corresponding to six types of phase components by one radiographing operation, but the structure of charge collection electrode shown in FIG. 24 allows the use of wider linear electrodes in comparison with the structure of FIG. 23. The spatial resolution is somewhat degraded in the structure shown in FIG. 24, but the structure allows easy connection of linear electrodes.

As described above, it is preferable that each radiation sources 1a emits radiation such that the exposure range at the position of subject 10 is arranged without any space and at an angle that substantially does not influence the diffraction properties of diffraction grating 25 and periodic information imaging radiation image detector 45 at peripheral portions of exposure range at the positions of diffraction grating 25 and periodic information imaging radiation image detector 45. Hereinafter, the angle will be discussed. Here, the allowable range of the angle will be discussed in terms of the positional displacement of a linear electrode group of periodic information imaging radiation image detector 45.

Figure 25:
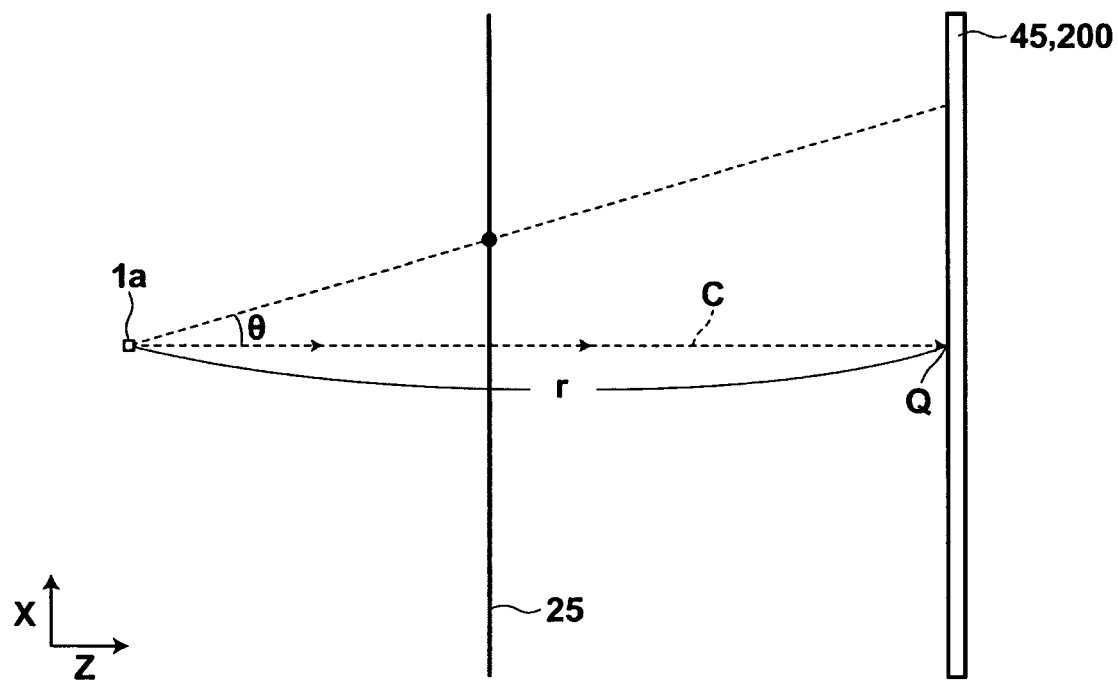
FIG. 25 illustrates conditions of spread angle of radiation emitted from a radiation source.

Assuming a required pitch of diffraction members at a position (r, x) away from intersection point Q between central axis C of radiation emitted from radiation source 1a and periodic information imaging radiation image detector 45 by distance x in a direction orthogonal to the diffraction members to be $\Delta x$, $\Delta x$ can be represented by Formula (10) below (FIG. 25, which is a top view of the phase image radiographing apparatus shown in FIG. 14. The thickness direction in FIG. 25 corresponds to Y direction in FIG. 14.)

$$\Delta x = r\Delta\theta \times \frac{\tan\theta}{\theta} \times \left\{ \sqrt{(r^2+x^2)} \times \frac{1}{r} \right\} \times \frac{1}{\cos\theta} \quad (10)$$

where, r is the distance from radiation source 1a (if a slit is used in the radiation emission unit, to be described later, from the position of the slit) to periodic information imaging radiation image detector 45, and $r\Delta\theta$ is the pitch of the linear electrodes at intersection point Q between the central axis C of the radiation beam and periodic information imaging radiation image detector 45.

Here, $x/r=\tan\theta$, which is substituted to Formula (10) above, then $\Delta x$ can be represented by Formula (11) below.

$$\Delta x = r\Delta\theta \times \frac{\tan\theta}{\theta} \times \frac{\sqrt{1+\tan^2\theta}}{\cos\theta} = r\Delta\theta \times \frac{\tan\theta}{\theta\cos^2\theta} \quad (11)$$

Thus, the ratio between the pitch at (r, x) and the pitch $r\Delta\theta$ at intersection point Q can be represented by Formula (12) below.

$$\frac{\Delta x}{r\Delta\theta} = \frac{\tan\theta}{\theta\cos^2\theta} \quad (12)$$

Relationship between $\theta$ and $\Delta x/r\Delta\theta$ obtained based on Formula (12) above is summarized in Table 2 below.

TABLE 2

| | $\theta$ | | | | |
|---|---|---|---|---|---|
| | 1.0° | 2.0° | 5.0° | 10.0° | 15.0° |
| $\Delta x/r\Delta\theta$ | 1.0004 | 1.002 | 1.01 | 1.04 | 1.10 |

Here, assuming that charge collection electrodes of periodic information imaging radiation image detector 45 are structured in the manner shown in FIG. 24, with pitch $P_2$ of the linear electrodes to be 0.8 μm and a line width of the linear electrode to be 3 μm, the width of linear electrode group for detecting a signal corresponding to one phase component is 35 μm and one pixel has a width of about 120 μm.

If the phase of each linear electrode group is shifted about 1/12 of the pitch, it is thought to be undesirable that a signal of different phase component is mixed in the same pixel. Given that the radiation beam spreads from the central axis to X direction (direction orthogonal to the diffraction members), it is preferable that the positional displacement of linear electrodes within one pixel is limited to 8/12×1/2=8/24=0.333 μm or less.

If the pitch of the linear electrodes on central axis C is 8 μm, the distance between the centers of linear electrodes at each end of linear electrode groups in a peripheral portion of the radiation beam is $\Delta x/r\Delta\theta \times 8 \times 4$.

Accordingly, if $\Delta x/r\Delta\theta \times 8 \times 4 - 32 < 0.333$, the condition described above is met.

Thus, $\Delta x/r\Delta\theta < 1.010$.

Accordingly, it is known from Table 2 above that one-side spread angle $\theta$ of the radiation beam in X direction needs to be limited to 5° or less.

For example, if r=1000 mm, 2×1000×tan 5°=175 mm, thus the width of radiation beam emitted from one radiation source 1a in X direction on periodic information imaging radiation image detector 45 needs to be limited to 175 mm or less.

So far, the description has been made of a case in which the charge collection electrode is divided into three sub-pixels as shown in FIG. 24. Now, the discussion will be made of a case in which the charge collection electrode is divided into two sub-pixels and two linear electrode groups are disposed in each sub-pixel so as to have a phase difference of $\pi$ from each other. Here, it is assumed that each linear electrode group has five linear electrodes, and the pitch and width of the linear electrodes are identical to those described above.

In this case, if the phase of each linear electrode group is shifted about 1/8 of the pitch, it is thought to be undesirable that a signal of different phase component is mixed in the same pixel. Given that the radiation beam spreads from the central axis to X direction (direction orthogonal to the linear electrodes), it is preferable that the positional displacement of linear electrodes in one pixel is limited to $8/8 \times 1/2 = 8/16 = 0.5$ μm or less.

If the pitch on central axis C is assumed to be 8 μm, the distance between the centers of linear electrodes at each end of linear electrode groups in a peripheral portion of the radiation beam is $\Delta x/r\Delta\theta \times 8 \times 4$.

Accordingly, if $\Delta x/r\Delta\theta \times 8 \times 4 - 32 < 0.5$, the condition described above is met.

Thus, $\Delta x/r\Delta\theta < 1.016$.

Accordingly, it is known from Table 2 above that one-side spread angle θ of the radiation beam in X direction needs to be limited to 6° or less.

For example, if r=1000 mm, $2 \times 1000 \times \tan 6° = 210$ mm, thus the width of radiation beam emitted from one radiation source 1a in X direction on periodic information imaging radiation image detector 45 needs to be limited to 210 mm or less.

The above discussion shows that the pitch of the linear electrodes does not depend on the restrictions of spread angle of the radiation beam.

Figure 26:
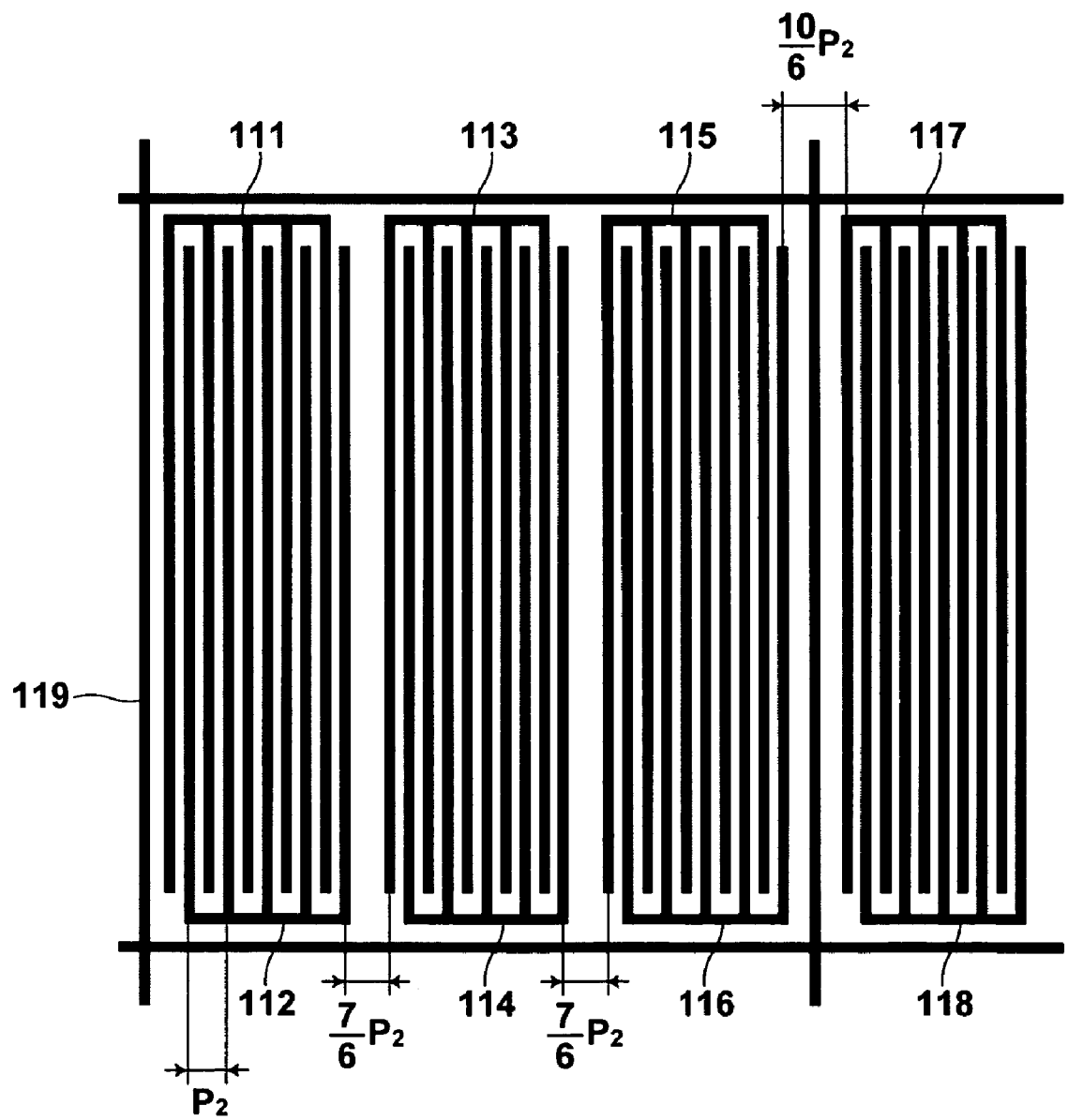
FIG. 26 illustrates a modification of the periodic information imaging radiation image detector in the tomosynthesis radiographing apparatus according to the third embodiment.

In addition to first to sixth linear electrode groups 111 to 116 shown in FIG. 24, constant potential electrode 119 may be provided in a grid pattern enclosing the charge collection electrode, constituted by first to sixth linear electrodes 111 to 116, of each unit element 72, as illustrated in FIG. 26. The effect of the constant potential electrode 119 is identical to that described in relation to FIG. 22. A potential that does not cause a large potential difference with an adjacent charge collection electrode is applied to constant potential electrode 119. That is, substantially the same potential as that of the charge collection electrode is applied. More specifically, constant potential electrode 119 is set to a ground potential or a value close to the ground potential. Where constant potential electrode 119 is provided, the pitch between linear electrode groups of adjacent pixels in a direction orthogonal to the linear electrodes, i.e., between linear electrode group 116 and linear electrode group 117, is set to $(10/6) \times P_2$, as shown in FIG. 26.

Figure 27:
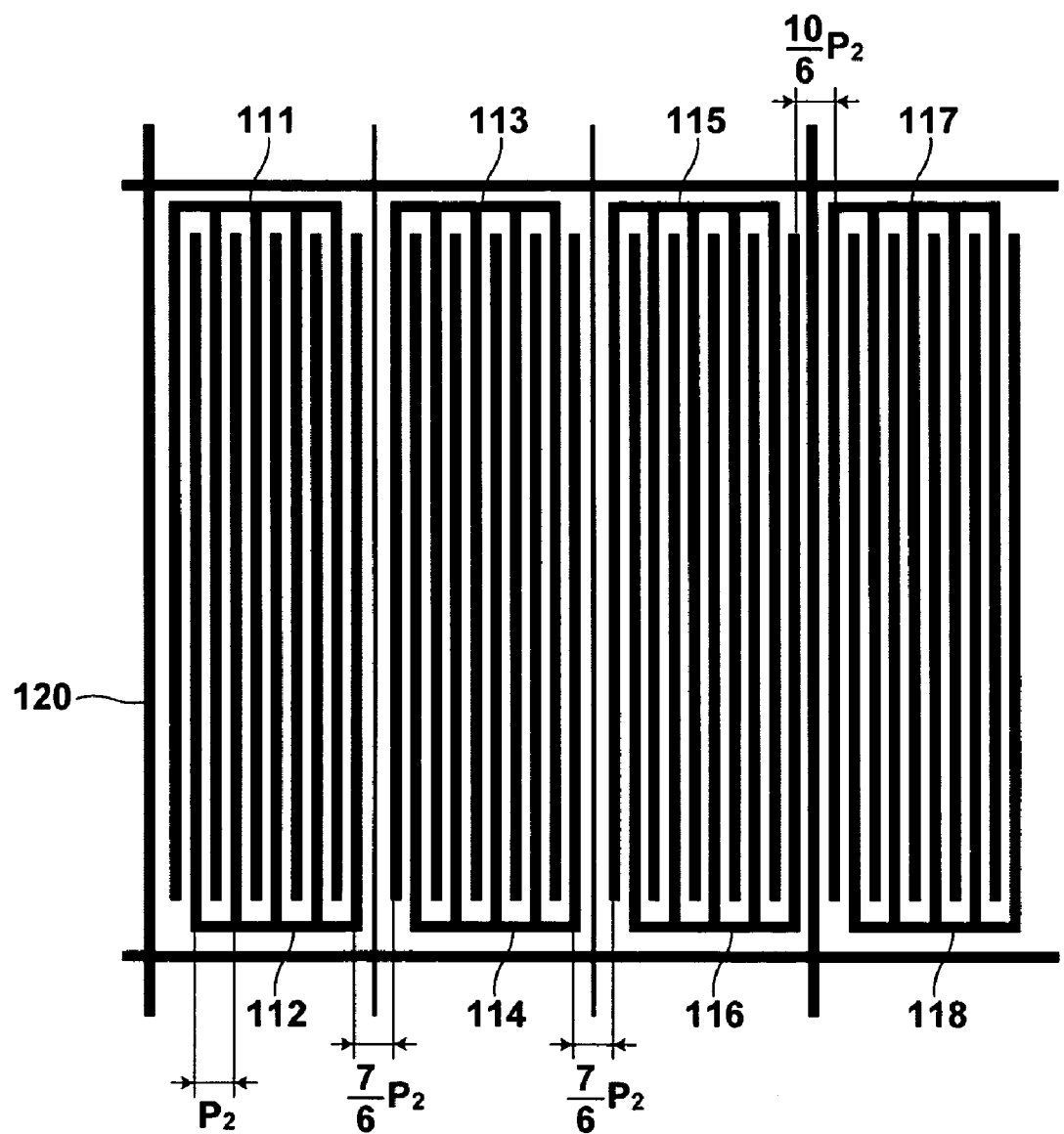
FIG. 27 illustrates a modification of the periodic information imaging radiation image detector in the tomosynthesis radiographing apparatus according to the third embodiment.

Instead of providing constant potential electrode 119 to enclose each pixel, as shown in FIG. 26, constant potential electrode 120 may be provided to enclose each sub-pixel, as shown in FIG. 27.

Figure 28:
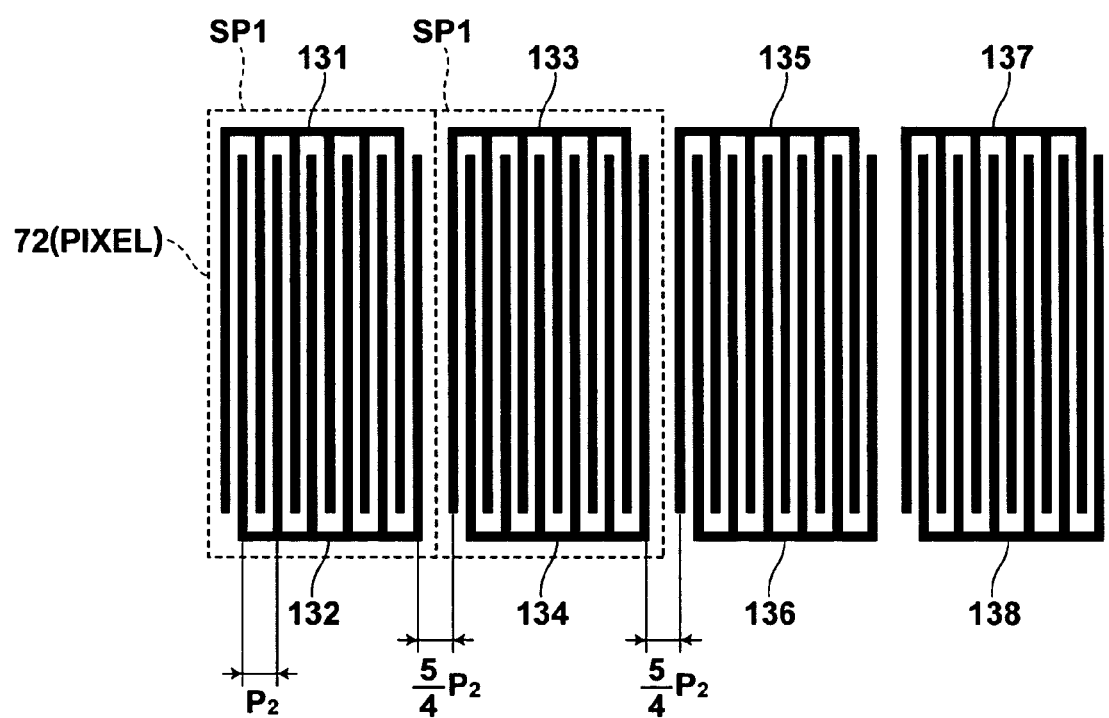
FIG. 28 illustrates a modification of the periodic information imaging radiation image detector in the tomosynthesis radiographing apparatus according to the third embodiment.

Further, as illustrated in FIG. 28, a pixel corresponding to one unit element 72 may be divided into two sub-pixels, and linear electrode groups having different phases may be disposed in each sub-pixel. More specifically, in the modification shown in FIG. 28, first linear electrode group 131 in which linear electrodes are arranged with pitch $P_2$ and second linear electrode group 132 in which linear electrodes are arranged with pitch $P_2$ are disposed in sub-pixel SP1 so as to have a phase difference of π from each other, third linear electrode group 133 in which linear electrodes are arranged with pitch $P_2$ and fourth linear electrode group 134 in which linear electrodes are arranged with pitch $P_2$ are disposed in sub-pixel SP2 so as to have a phase difference of π from each other. Then, adjacent linear electrode groups of sub-pixel SP1 and sub-pixel SP2 are disposed at a distance of $(5/4) \times$pitch $P_2$. This arrangement results in that, when the phase of first linear electrode group 131 is 0, the phase of second linear electrode group 132 is π, the phase of third linear electrode group 133 is $3\pi/2$, the phase of fourth linear electrode group 134 is $\pi/2$, that is, first to fourth linear electrode groups correspond to the phases shifted by $\pi/2$ from each other. Linear electrode groups 135 to 138 are linear electrode groups of adjacent pixels. Linear electrode group 135 detects a signal having the same phase as that of first linear electrode group 131, linear electrode group 136 detects a signal having the same phase as that of second linear electrode group 132, linear electrode group 137 detects a signal having the same phase as that of third linear electrode group 133, and linear electrode group 138 detects a signal having the same phase as that of fourth linear electrode group 134.

Formation of the charge collection electrode in the manner illustrated in FIG. 28 to read out charges collected by first to fourth linear electrode groups 131 to 134 with respect to each linear electrode group allows acquisition of image signals corresponding to four types of phase components by one radiographing operation.

FIG. 24 or 28 illustrates a case where a pixel corresponding to one unit element 72 is divided into three or two sub-pixels, but the pixel may be divided into n (n≧4) sub-pixels. In this case, if the pitch between adjacent linear electrode groups of adjacent sub-pixels is set to $(2n+1)P_2/2n$, linear electrode groups corresponding to phases shifted by $\pi/n$ from each other may be provided.

When a pixel is divided into two to three sub-pixels, data of four to six phase components may be obtained by one radiographing operation, and a preferable phase image may be formed. When obtaining data of four to six phase components without dividing a pixel into sub-pixels, the structure shown in FIG. 23 may be used, but each linear electrode has a narrow width, which may cause a manufacturing problem. On the other hand, n≧4 while maintaining the pixel size causes each linear electrode group to have a less number of linear electrodes, whereby the accuracy as the data of phase components is degraded.

When diving a pixel into a plurality of sub-pixels in the manner as described above, it is preferable to set the width of the pair of linear electrode groups in the length direction of the linear electrodes in each sub-pixel greater than the width of the pair of linear electrode groups in a direction orthogonal to the length direction of the linear electrodes, as illustrated in FIGS. 24, and 26 to 28.

Figure 29:
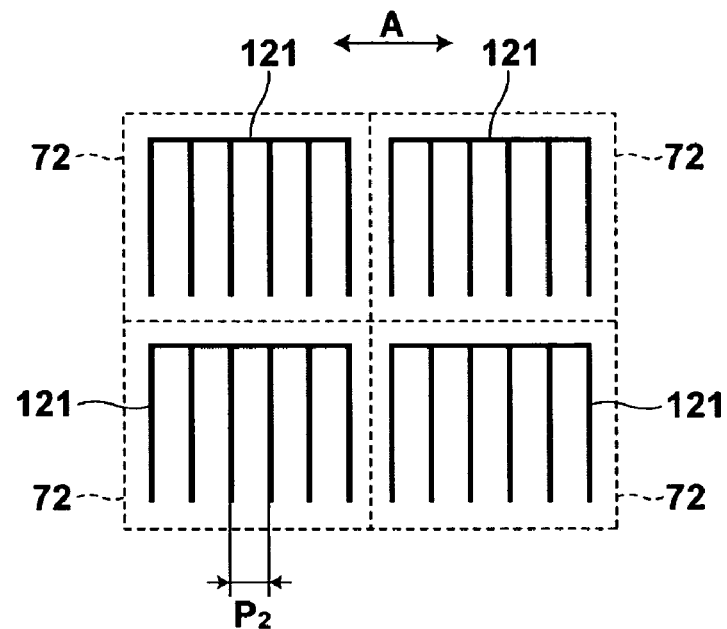
FIG. 29 illustrates a modification of the periodic information imaging radiation image detector in the tomosynthesis radiographing apparatus according to the third embodiment.

The modification described above is an example in which a plurality of linear electrode groups is provided in each unit element 72. But, for example, only one linear electrode group 121, in which linear electrodes are arranged with pitch $P_2$, may be provided in each unit element 72, as illustrated in FIG. 29. FIG. 29 illustrates linear electrode groups 121 of four adjacent unit elements 72. As illustrated in FIG. 29, where the charge collection electrode of unit element 72 is formed of one linear electrode group and image signals corresponding to a plurality of types of phase components having different phases are obtained, a shifting mechanism for shifting periodic information imaging radiation image detector 45 and diffraction grating 25 in a direction orthogonal to linear electrodes (arrow A direction in FIG. 29) along the respective planes may be provided and radiation image taking may be performed a plurality of times by shifting detector 45 and grating 25. For example, image signals corresponding to three types of phase components may be obtained by shifting detector 40 and grating 20 by 1/3 of pitch $P_2$ and taking a radiation image at each position. Otherwise, image signals corresponding to six types of phase components may be obtained by shifting detector 40 and grating 20 by 1/6 of pitch $P_2$ and taking a radiation image at each position.

Figure 30:
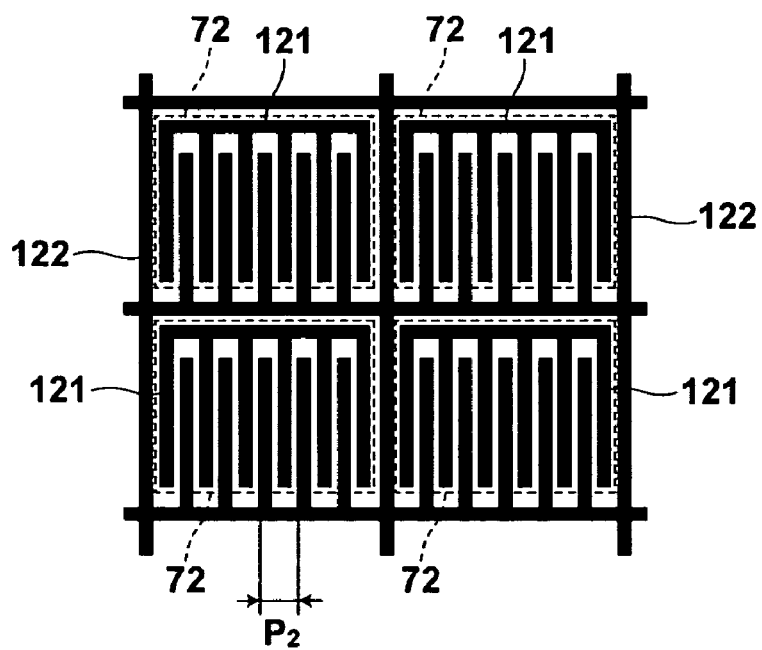
FIG. 30 illustrates a modification of the periodic information imaging radiation image detector in the tomosynthesis radiographing apparatus according to the third embodiment.

In addition to the charge collection electrodes of linear electrode groups 121 shown in FIG. 29, constant potential electrode 122 may be provided as illustrated in FIG. 30. Constant potential electrode 122 is arranged so as to be disposed between each linear electrode of each linear electrode group 121 and in a grid pattern to enclose each unit element 72. The effect of the constant potential electrode 122 is identical to that described in relation to FIG. 22. A potential that does not cause a large potential difference with an adjacent charge collection electrode is applied to constant potential electrode 122. That is, substantially the same potential as that of the charge collection electrode is applied. More specifically, constant potential electrode 122 is set to a ground potential or a value close to the ground potential.

In FIG. 20, the description has been made of a case in which first linear electrode group 81a and second linear electrode group 81b are phase shifted by $\pi$ from each other, but instead, three linear electrode groups phase shifted by $2\pi/3$ from each other may be provided in each unit element 72. If the charge collection electrode of each unit element 72 is formed of three linear electrode groups in the manner as described above and periodic information imaging radiation image detector 45 and diffraction grating 25 are shifted, for example, by ½ of pitch $P_2$ to take a radiation image at each position, image signals corresponding to six types of phase components may be obtained.

In the tomosynthesis radiographing apparatus according to the third embodiment, a radiation image detector having TFT switches is used, but a CMOS or a CCD may also be used as the switch element.

Further, in the tomosynthesis radiographing apparatus according to the third embodiment, periodic information imaging radiation image detector 45 to which a positive voltage is applied when recording a radiation image is used. Alternatively, a TFT readout type radiation image detector to which a negative voltage is applied when recording a radiation image may be used.

Next, a fourth embodiment of the tomosynthesis radiographing apparatus of the present invention will be described. The tomosynthesis radiographing apparatus according to the fourth embodiment uses an optical readout type periodic information imaging radiation image detector, instead of the TFT readout type periodic information imaging radiation image detector of the phase image radiographing apparatus according to the third embodiment. The tomosynthesis radiographing apparatus according to the fourth embodiment differs from the tomosynthesis radiographing apparatus according to the third embodiment only in the structure of the periodic information imaging radiation image detector. Accordingly, only the structure of the periodic information imaging radiation image detector will be described. FIG. 31A is a perspective view of the periodic information imaging radiation image detector, FIG. 31B is an XZ sectional view of the periodic information imaging radiation image detector shown in FIG. 31A, and FIG. 31C is an XY sectional view of the periodic information imaging radiation image detector shown in FIG. 31A.

As illustrated in FIGS. 31A to 31C, periodic information imaging radiation image detector 200 of the tomosynthesis radiographing apparatus according to the third embodiment includes the following stacked in the order listed below: first electrode layer 201 that transmits radiation; recording photoconductive layer 202 that generates charges by receiving radiation transmitted through first electrode layer 201; charge transport layer 204 that acts as an insulator against charges of one polarity of those generated in recording photoconductive layer 202 and as a conductor for charges of the other polarity; readout photoconductive layer 205 that generates charges by receiving readout light; and second electrode layer 206. Storage section 203 for storing charges generated in recording photoconductive layer 202 is formed adjacent to the interface between recording photoconductive layer 202 and charge transport layer 204. Each of the layers described above is stacked on glass substrate 207 one after another from second electrode layer 206.

First electrode layer 201 may be made of any material as long as it transmits radiation. For example, a NESA film ($SnO_2$), ITO (Indium Tin Oxide), IZO (Indium Zinc Oxide) IDIXO (Idemitsu Indium X-metal Oxide: Idemitsu Kosan Co., Ltd), or the like, formed into a thickness of 50 to 200 nm, may be used. Alternatively, Al or Au of 100 nm thickness may be used.

Second electrode layer 206 includes a plurality of transparent linear electrodes 206a that transmits readout light and a plurality of opaque linear electrodes 206b that blocks the readout light. Transparent linear electrodes 206a and opaque linear electrodes 206b extend from one end of an image forming area of periodic information imaging radiation image detector 200 to the other end continuously and straightly. As illustrated in FIGS. 31A and 31B, transparent linear electrodes 206a and opaque linear electrodes 206b are disposed alternately in parallel at a predetermined distance.

Transparent linear electrodes 206a are formed of a material that transmits readout light and has conductivity. For example, ITO, IZO, or IDIXO may be used as in first electrode layer 201. The thickness of each electrode 206a is about 100 to 200 nm.

Opaque linear electrodes 206b are formed of a material that blocks the readout light and has conductivity. It is preferable that opaque linear electrodes 206b transmit erasure light, and a combination of one of the transparent conductive materials described above with a color filter is used as the opaque linear electrode 206b. The thickness of the transparent conductive material is about 100 to 200 nm.

As will be described later, an image signal is read out by adjacent transparent linear electrode 206a and opaque linear electrode 206b as a pair. In periodic information imaging radiation image detector 200 of the present embodiment, 20 pairs of transparent linear electrode 206a and opaque linear electrode 206b are disposed in the width of one pixel constituting a radiation image, as illustrated in FIG. 32. That is, 20 linear electrode pairs from first linear electrode pair 211, second linear electrode pair 212, third linear electrode pair 213, and so forth are disposed within the width of one pixel. In the present invention, the term "pixel unit" in the fourth embodiment refers to a segment in a direction orthogonal to the linear electrodes.

As illustrated in FIG. 32, the linear electrode pairs are disposed such that the distance between every other pairs, e.g., the distance between first linear electrode pair 211 and third linear electrode pair 213, or the distance between second linear electrode pair 212 and fourth linear electrode pair 214, corresponds to pitch $P_2$. Pitch $P_2$ is set to a value in the range from 2 to 15 µm. A first linear electrode group is formed of $(2n-1)^{th}$ (n is an integer not smaller than 1 and not greater than 10) linear electrode pair and a second linear electrode group is formed of $(2n)^{th}$ (n is an integer not smaller than 1 and not greater than 10) linear electrode pair.

Then, the first and second linear electrode groups within the width of one pixel described above are alternately disposed in a direction orthogonal to the length direction of the linear electrodes. In this case, the first electrode group and second linear electrode group are disposed so as to be phase shifted by $\pi$ from each other. Although not shown, transparent linear electrodes 206a of the first linear electrode groups are physically connected to each other with a connection wire, such as a lead wire. Also, transparent linear electrodes 206a of the second linear electrode groups are physically connected to each other with a connection wire, such as a lead wire.

Recording photoconductive layer 202 may be formed of any material as long as it generates charges when exposed to radiation. Here, a-Se based material having excellent properties, such as relatively high quantum efficiency to radiation and high dark resistance, is used. An appropriate layer thickness is in the range from 10 to 1500 µm. For a mammography application, in particular, a preferable layer thickness is in the range from 150 to 250 µm, and for a general radiography application, a preferable layer thickness is in the range from 500 to 1200 µm.

As for the material of charge transport layer 204, for example, a material having a greater difference in charge mobility between charges charged on first electrode layer 201 when a radiation image is recorded and the charges having opposite polarity (for example, not less than $10^2$, more preferably, not less than $10^3$), is preferably used. In this respect, organic compounds such as polyN-vinylcarbazole (PVK), N,N'-diphenyl-N,N'-bis (3-methylphenyl)-[1,1'-biphenyl]-4,4'-diamine(TPD), discotic liquid crystal, and the like, or semiconductor materials such as TPD-dispersed polymers (polycarbonate, polystyrene, PVK), a-Se doped with 10 to 200 ppm of Cl, $As_2Se_3$, and the like are preferably used. An appropriate thickness of charge transport layer is in the range from 0.2 to 2 µm.

Readout photoconductive layer 205 may be formed of any material as long as it shows conductivity when exposed to readout light. For example, a photoconductive material consisting primarily of at least one of a-Se, Se—Te, Se—As—Te, non-metal phthalocyanine, metal phthalocyanine, MgPc (magnesium phthalocyanine) VoPc (phase II of Vanadyl phthalocyanine, CuPc (cupperphthalocyanine), and the like is preferably used. An appropriate thickness of photoconductive layer 205 is in the range from 5 to 20 µm.

Next, an operation for recording a radiation image to and reading out from the periodic information imaging radiation image detector of the tomosynthesis radiographing apparatus according to the fourth embodiment will be described.

The operational steps from the emission of radiation from radiation emission unit 1 to the formation of self-image by diffraction grating 25 are identical to those of the tomosynthesis radiographing apparatus according to the third embodiment, and therefore will not be elaborated upon further here.

Figure 33A:
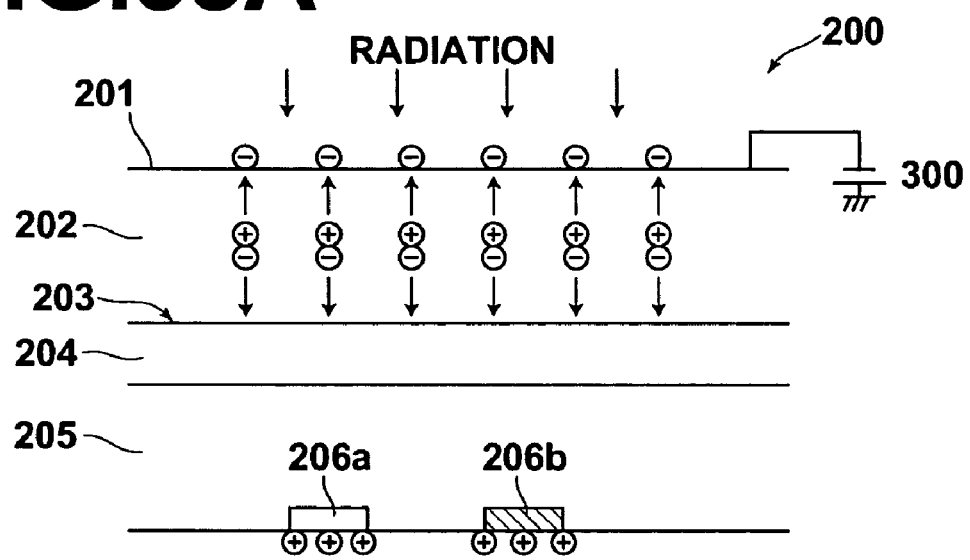
FIGS. 33A and 33B illustrate a recording operation for recording a radiation image in the periodic information imaging radiation image detector in the fourth embodiment of the tomosynthesis radiographing apparatus of the present invention.

Then, as illustrated in FIG. 33A, with a negative voltage being applied to first electrode layer 201 of periodic information imaging radiation image detector 200 by high voltage source 300, radiation representing a self-image formed by Talbot effect of diffraction grating 25 is emitted to periodic information imaging radiation image detector 200 from the side of first electrode layer 201.

Figure 33B:
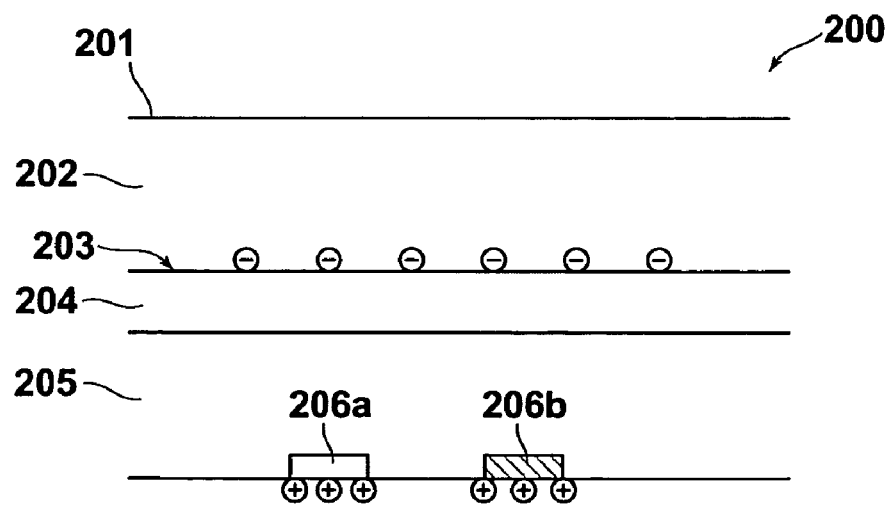

The radiation emitted to periodic information imaging radiation image detector 200 transmits through first electrode layer 201 and irradiates recording photoconductive layer 202. Then, recording photoconductive layer 202 generates charge pairs by the irradiation of the radiation, and positive charges of the charge pairs are combined with negative charges charged on the first electrode layer 201 and dissolved, while negative charges of the charge pairs are stored, as latent image charges, in storage section 203 formed at the interface between recording photoconductive layer 202 and charge transport layer 204 (FIG. 33B).

Here, in periodic information imaging radiation image detector 200 of tomosynthesis radiographing apparatus of the present embodiment, second electrode layer 206 for collecting charges generated in recording photoconductive layer 202 to storage section 203 is constituted by transparent linear electrode 206a and opaque linear electrode 206b. Therefore, when a voltage is applied to first electrode layer 201 in the manner as described above, electric fields are formed in recording photoconductive layer 202 from transparent linear electrode 206a and opaque linear electrode 206b toward first electrode layer 201 substantially parallel to each other, i.e., substantially perpendicular to the surface of first electrode layer 201. Negative charges generated in recording photoconductive layer 202 are shifted toward each linear electrode along the electric field without spreading and collected in storage section 203, so that transparent linear electrode 206a and opaque linear electrode 206b perform a function equivalent to that of the combination of an amplitude diffraction grating and a detector provided in the later stage of the grating. Accordingly, charges representing image contrast generated by the superimposition of a self-image of the deformed diffraction grating 25 and a virtual diffraction grating formed by the first linear electrode group are stored in a portion of storage section 203 above the first linear electrode group constituted by $(2n-1)^{th}$ (n is an integer not smaller than 1 and not greater than 10) linear electrode pair shown in FIG. 32 and charges representing image contrast generated by the superimposition of a self-image of the deformed diffraction grating 25 and a virtual diffraction grating formed by second linear electrode group are stored in a portion of storage section 203 above the second linear electrode group constituted by $2n^{th}$ (n is an integer not smaller than 1 and not greater than 10) linear electrode pair shown in FIG. 32. The image contrast described above generally takes the form of Moire fringes. As described above, the first linear electrode group and second linear electrode group are phase shifted by π from each other, thus signals corresponding to two types of phase components phase shifted from each other by π are recorded in periodic information imaging radiation image detector 200.

Figure 34:
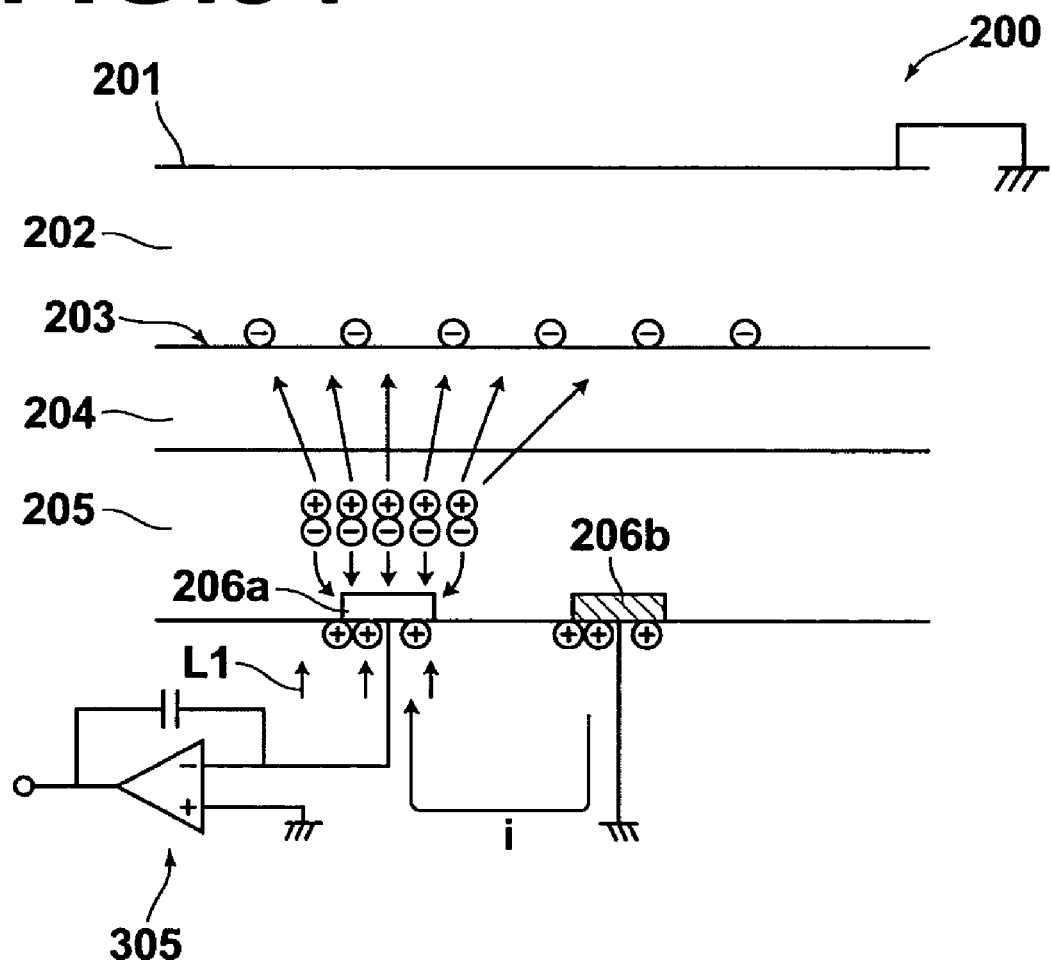
FIG. 34 illustrates a reading operation for reading out a radiation image from the periodic information imaging radiation image detector in the fourth embodiment of the tomosynthesis radiographing apparatus of the present invention.

Then, with the first electrode layer 201 being grounded, readout light L1 is emitted from the side of second linear electrode layer 206, as illustrated in FIG. 34. Readout light L1 transmits through transparent linear electrodes 206a and irradiates readout photoconductive layer 205. Positive charges generated in readout photoconductive layer 205 combine with latent image charges in storage section 203 while negative charges combine with positive charges charged on opaque linear electrode 206b through charge amplifier 305 connected to opaque linear electrode 206b.

A current flows through charge amplifier 305 when the negative charges generated in readout photoconductive layer 205 are combined with the positive charges charged on opaque linear electrode 206b, and the current is integrated and detected as an image signal.

At this time, charges, flowed out from the first linear electrode group of first linear electrode pair 211 and third linear electrode pair 213 shown in FIG. 32, are detected by charge amplifier 305 as an image signal corresponding to a first phase component. In the mean time, charges, flowed out from the second linear electrode group of second linear electrode pair 212 and fourth linear electrode pair 214 shown in FIG. 32, are detected by charge amplifier 305 as an image signal corresponding to a second phase component.

Thereafter, periodic information imaging radiation image detector 200 is shifted by shifting mechanism 55, and the image recording in the detector 40 and image signal reading from the detector 200 are performed at each predetermined position, whereby image signals corresponding to the first and second phase components are detected at each predetermined position.

Image signals detected in the manner as described above are inputted to phase image generation unit 65. Then, phase image generation unit 65 generates a partial phase image with respect to each detection area of periodic information imaging radiation image detector 200 based on image signals of a plurality of phase components detected by periodic information imaging radiation image detector 200 in each detection area corresponding to the exposure range of radiation emitted from each radiation source 1*a*. That is, a partial phase image corresponding to each radiation source 1*a* is generated. Thereafter, the partial phase images are combined to produce a complete phase image.

Then, radiation emission unit 1 is shifted in Y direction, as in the third embodiment; and at each predetermined position, radiation is emitted from each radiation source 1*a* of radiation emission unit 1 and diffraction grating 25 and periodic information imaging radiation image detector 200 are shifted, whereby a phase image at each position of radiation emission unit 1 is sequentially generated.

Image signals representing a plurality of phase images generated in phase image generation unit 65 are inputted to tomographic image generation unit 4. Tomographic image generation unit 4 performs shift processing on the inputted plurality of image signals according to a desired cross-sectional position of the subject and generates a tomographic image according to the cross-sectional position by adding the shift processed image signals, as in the third embodiment.

For example, in the tomosynthesis radiographing apparatus of the fourth embodiment, image signals corresponding to six types of phase components may be obtained by shifting detector 200 and grating 25 by ⅓ of pitch $P_2$ in a direction orthogonal to the linear electrodes along the respective planes by diffraction grating shifting mechanism 55 and taking a radiation image at each position.

Also, in the tomosynthesis radiographing apparatus of the fourth embodiment, linear electrode group pairs, in which respective linear electrode groups are disposed in order, may be disposed to different positions so as to have different phases as in the periodic information imaging radiation image detector of third embodiment. This allows image signals corresponding to sufficient number of phase components for forming a phase image to be obtained at the same time without requiring the shifting mechanism.

As described above, it is preferable that each radiation sources 1*a* emits radiation such that the exposure range at the position of subject 10 is arranged without any space and at an angle that substantially does not influence the diffraction properties of diffraction grating 25 and linear electrode groups of periodic information imaging radiation image detector 200 at peripheral portions of exposure ranges at the positions of diffraction grating 25 and periodic information imaging radiation image detector 200. Hereinafter, the angle will be discussed. Here, the allowable range of the angle will be discussed in terms of the positional displacement of linear electrodes of periodic information imaging radiation image detector 200.

Assuming a required pitch of linear electrodes at a position (r, x) away from intersection point Q between central axis C of radiation emitted from radiation source 1*a* and periodic information imaging radiation image detector 200 by distance x in a direction orthogonal to the linear electrodes to be Δx, Δx can be represented by Formula (13) below (FIG. 25, which is a top view of the phase image radiographing apparatus shown in FIG. 14. The thickness direction in FIG. 24 corresponds to Y direction in FIG. 14.)

$$\Delta x = r\Delta\theta \times \frac{\tan\theta}{\theta} \times \left\{\sqrt{(r^2+x^2)} \times \frac{1}{r}\right\} \times \frac{1}{\cos\theta} \qquad (13)$$

where, r is the distance from radiation source 1*a* (if a slit is used in the radiation emission unit, to be described later, from the position of the slit) to periodic information imaging radiation image detector 200, and rΔθ is the pitch of the linear electrodes at intersection point Q between the central axis C of the radiation beam and periodic information imaging radiation image detector 200.

Here, x/r=tan θ, which is substituted to Formula (13) above, then Δx can be represented by Formula (14) below.

$$\Delta x = r\Delta\theta \times \frac{\tan\theta}{\theta} \times \frac{\sqrt{1+\tan^2\theta}}{\cos\theta} = r\Delta\theta \times \frac{\tan\theta}{\theta\cos^2\theta} \qquad (14)$$

Thus, the ratio between the pitch at (r, x) and the pitch rΔθ at intersection point Q can be represented by Formula (15) below.

$$\frac{\Delta x}{r\Delta\theta} = \frac{\tan\theta}{\theta\cos^2\theta} \qquad (15)$$

Relationship between θ and Δx/rΔθ obtained based on Formula (15) above is summarized in Table 3 below.

TABLE 3

| | θ | | | | |
|---|---|---|---|---|---|
| | 1.0° | 2.0° | 5.0° | 10.0° | 15.0° |
| Δx/rΔθ | 1.0004 | 1.002 | 1.01 | 1.04 | 1.10 |

Here, if Pitch $P_2$ of linear electrode pair of periodic information imaging radiation image detector 200 is 8 μm and the line width of each linear electrode is 3 μm, the width of one pixel is about 80 μm.

If the phase of each linear electrode pair is shifted about ⅛ of the pitch, it is thought to be undesirable that a signal of different phase component is mixed in the same pixel. Given that the radiation beam spreads from the central axis to X direction (direction orthogonal to the linear electrodes), it is preferable that the positional displacement of linear electrode pair within one pixel is limited to 8/8×1/2=8/16=0.5 μm or less.

If the pitch of the linear electrode pair on central axis C is 8 μm, the distance between the centers of linear electrode pairs at each end of a pixel in a peripheral portion of the radiation beam is Δx/rΔθ×8×9.

Accordingly, if Δx/rΔθ×8×9−72<0.5, the condition described above is met.

Thus, Δx/rΔθ<1.007.

Accordingly, it is known from Table 3 above that one-side spread angle θ of the radiation beam in X direction needs to be limited to 2° or less.

For example, if r=1000 mm, 2×1000×tan 2°=70 mm, thus the width of radiation beam emitted from one radiation source 1*a* in X direction on periodic information imaging radiation image detector 200 needs to be limited to 70 mm or less.

In the tomosynthesis radiographing apparatus according to the fourth embodiment, periodic information imaging radiation image detector 200 to which a negative voltage is applied when recording a radiation image is used. Alternatively, an optical readout type periodic information imaging radiation image detector to which a positive voltage is applied when recording a radiation image may be used.

In the tomosynthesis radiographing apparatuses according to the third and fourth embodiments, the description has been made of a case in which subject 10 is placed between radiation emission unit 1 and diffraction grating 25. When subject 10 is placed between diffraction grating 25 and periodic information imaging radiation image detector 45 or 200, the self-image of diffraction grating 25 produced at the position of periodic information imaging radiation image detector 45 or 200 is deformed by subject 10. Therefore, also in this case, an image signal of a phase component modulated due to subject 10 can be detected by periodic information imaging radiation image detector 45 or 200. That is, in the tomosynthesis radiographing apparatus according to the third or fourth embodiment, subject 10 may be placed between radiation emission unit 1 and diffraction grating 25 or between diffraction grating 25 and periodic information imaging radiation image detector 45 or 200.

As described above, in the third and fourth embodiments, radiation emission unit 1 may be structured in various ways as described in the first and second embodiments. When using a radiation emission unit having multi-slit 16d shown in FIG. 10, however, it is necessary to dispose the multi-slit so as to become parallel to diffraction members of diffraction grating 25 and linear electrodes. Further, it is preferable that radiation emission unit 1 is a unit that limits each radiation exposure range such that each exposure range of radiation passed through the collimator overlap with each other without any space between them at a position of subject 10 and at an angle that substantially does not influence a diffraction property of diffraction grating 25 in a peripheral portion of an exposure range at the position of diffraction grating 25.

In radiation emission unit 16 shown in FIG. 10, when metal target 16c is formed with metal wires, the wires need to be arranged so as to become parallel to diffraction members 22 of diffraction grating 25 and linear electrodes.

Further, in radiation emission unit 16 shown in FIG. 10, when cold cathode electron source 16a is formed with linear cold cathode electron sources, the linear cold cathode electron sources need to be arranged so as to become parallel to diffraction members of diffraction grating 25 and linear electrodes.

When the structure shown in FIG. 10 or any other modifications thereof described above is used, a Talbot-Lau interferometer is formed.

What is claimed is:

1. A tomosynthesis radiographing apparatus, comprising;
a radiation emission unit having multiple radiation sources for emitting radiation onto a subject, the radiation sources being distributed such that radiation emitted from each radiation source and transmitted through the subject forms a part of a projected image of the subject;
a radiation image detector for detecting radiation emitted from each radiation source of the radiation emission unit; and
a tomographic image generation unit for generating a tomographic image of the subject based on detection information detected by the radiation image detector when radiation is emitted onto the subject from different positions by the radiation emission unit,
wherein each radiation source emits fan beam radiation and is disposed such that a plane of the fan beam having a wider spread angle intersects with an arrangement direction of the multiple radiation sources and is arranged parallel to each other;
further comprising:
a first diffraction grating configured to be exposed to radiation emitted from the multiple radiation sources of the radiation emission unit and to produce Talbot interference or Talbot-Lau interference by the exposure; and
a second diffraction grating for diffracting radiation diffracted by the first diffraction grating, wherein:
the first diffraction grating is disposed such that an extension direction of a diffraction member constituting the first diffraction grating corresponds to a spreading direction of the fan beam in the plane having a wider spread angle and the second diffraction grating is disposed such that an extension direction of a diffraction member constituting the second diffraction grating corresponds to the spreading direction of the fan beam in the plane having a wider spread angle; and
the radiation image detector is a detector that detects radiation diffracted by the second diffraction grating.

2. The tomosynthesis radiographing apparatus of claim 1, wherein the spread angle of the fan beam in the plane having a wider spread angle is ten times or more of a spread angle of the fan beam in a direction orthogonal to the plane.

3. The tomosynthesis radiographing apparatus of claim 1, wherein:
the radiation emission unit is a unit constituted by the multiple radiation sources disposed in a line;
the apparatus further comprises a shifting mechanism for shifting the radiation emission unit along a plane opposite to a detection surface of the radiation image detector; and
the tomographic image generation unit is a unit that generates a tomographic image of the subject based on detection information detected by the radiation image detector when the radiation emission unit is shifted by the shifting mechanism and radiation is emitted onto the subject from different positions.

4. The tomosynthesis radiographing apparatus of claim 3, wherein:
the radiation emission unit is a unit constituted by the multiple radiation sources disposed in a line;
the shifting mechanism is a mechanism that shifts the radiation emission unit in a direction orthogonal to the line.

5. The tomosynthesis radiographing apparatus of claim 1, wherein:
the radiation emission unit is a unit constituted by the multiple radiation sources disposed two-dimensionally; and
radiation is emitted onto the subject from different positions by sequentially switching the radiation sources.

6. The tomosynthesis radiographing apparatus of claim 1, wherein:
the multiple radiation sources and the first diffraction grating are disposed such that spacing between the multiple radiation sources in a direction orthogonal to the extension direction of the diffraction member of the first diffraction grating is smaller than a distance from the radiation sources to the first diffraction grating; and
each of the multiple radiation sources is a source that emits radiation such that exposure ranges of adjacent radiation sources at a position of the subject overlap with each other without any space between them and at an angle that substantially does not influence a diffraction property of the first diffraction grating in a peripheral portion of an exposure range at a position of the first diffraction grating.

7. The tomosynthesis radiographing apparatus of claim 1, wherein:
the radiation emission unit is a unit that sequentially switches between certain radiation source groups and radiation source groups other than the certain radiation source groups of the multiple radiation sources disposed in a direction orthogonal to the plane of the fan beam having a wider spread angle to emit radiation from each radiation source group; and
radiation sources belonging to each radiation source group emit radiation such that exposure ranges of radiation emitted simultaneously from the radiation sources are separated from each other at a position of the radiation image detector.

* * * * *